(12) United States Patent
Wheeler et al.

(10) Patent No.: US 9,375,218 B2
(45) Date of Patent: *Jun. 28, 2016

(54) SYSTEMS AND METHODS OF TISSUE CLOSURE

(71) Applicant: DATASCOPE CORP., Mahwah, NJ (US)

(72) Inventors: William K. Wheeler, Berthoud, CO (US); Ashik A. Mohan, Petaluma, CA (US)

(73) Assignee: DATASCOPE CORP., Mahwah, NJ (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/047,832

(22) Filed: Oct. 7, 2013

(65) Prior Publication Data
US 2014/0214074 A1    Jul. 31, 2014

Related U.S. Application Data

(60) Continuation of application No. 13/180,373, filed on Jul. 11, 2011, now Pat. No. 8,561,872, which is a division of application No. 11/744,135, filed on May 3, 2007, now Pat. No. 7,992,757.

(60) Provisional application No. 60/797,461, filed on May 3, 2006.

(51) Int. Cl.
*A61B 17/068* (2006.01)
*A61B 17/122* (2006.01)
(Continued)

(52) U.S. Cl.
CPC ............. *A61B 17/122* (2013.01); *A61B 17/064* (2013.01); *A61B 17/0643* (2013.01); *A61B 17/072* (2013.01); *A61B 17/1285* (2013.01);
(Continued)

(58) Field of Classification Search
CPC ................................ A61B 17/068; A61F 2/00
USPC ............. 227/19, 175.1, 176.1, 180.1; 600/37; 606/139, 219, 220
See application file for complete search history.

(56) References Cited

U.S. PATENT DOCUMENTS

| | | | |
|---|---|---|---|
| 729,116 | A | 5/1903 | Barnstead |
| 1,756,670 | A | 4/1930 | Treat |

(Continued)

FOREIGN PATENT DOCUMENTS

| | | |
|---|---|---|
| CN | 1883411 A | 12/2006 |
| DE | 19520158 A1 | 12/1996 |

(Continued)

OTHER PUBLICATIONS

Amendment dated Jul. 22, 2011 for U.S. Appl. No. 13/117,863.
(Continued)

*Primary Examiner* — Nathaniel Chukwurah
(74) *Attorney, Agent, or Firm* — Wesley Scott Ashton; Kirk Swenson

(57) ABSTRACT

Apparatus, systems, and methods are described for closing the base of a left atrial appendage or other tissue structure. A tissue closure device comprises a pair of legs having compliant surfaces for engaging against opposite sides of the tissue structure. A plurality of axially spaced-apart tissue-penetrating fasteners are delivered from one leg to the other to pierce the intervening tissue and hold the closure device in place on the tissue structure.

16 Claims, 29 Drawing Sheets

(51) Int. Cl.
*A61B 17/064* (2006.01)
*A61B 17/072* (2006.01)
*A61B 17/128* (2006.01)
*A61B 17/00* (2006.01)
*A61B 17/30* (2006.01)

(52) U.S. Cl.
CPC .............. *A61B 2017/00243* (2013.01); *A61B 2017/07214* (2013.01); *A61B 2017/306* (2013.01)

(56) References Cited

U.S. PATENT DOCUMENTS

| | | |
|---|---|---|
| 2,659,371 A | 11/1953 | Schnee |
| 3,361,133 A | 1/1968 | Kimberley et al. |
| 3,525,340 A | 8/1970 | Gilbert et al. |
| 3,746,002 A | 7/1973 | Haller |
| 3,993,076 A | 11/1976 | Fogarty |
| 4,016,883 A | 4/1977 | Wright, Jr. |
| 4,060,089 A | 11/1977 | Noiles |
| 4,241,861 A | 12/1980 | Fleischer |
| 4,257,419 A | 3/1981 | Goltner et al. |
| 4,271,828 A | 6/1981 | Angelchik |
| 4,390,019 A | 6/1983 | LeVeen et al. |
| 4,402,445 A | 9/1983 | Green |
| 4,414,721 A | 11/1983 | Hufnagel |
| 4,487,205 A | 12/1984 | Di Giovanni et al. |
| 4,489,725 A | 12/1984 | Casey et al. |
| 4,506,670 A | 3/1985 | Crossley |
| 4,506,671 A | 3/1985 | Green |
| 4,548,201 A | 10/1985 | Yoon |
| 4,610,250 A | 9/1986 | Green |
| 4,702,247 A | 10/1987 | Blake et al. |
| 4,724,839 A | 2/1988 | Bedi et al. |
| 4,754,758 A | 7/1988 | Li |
| 4,805,617 A | 2/1989 | Bedi et al. |
| 4,822,348 A | 4/1989 | Casey |
| 4,924,864 A | 5/1990 | Danzig |
| 4,960,420 A | 10/1990 | Goble et al. |
| 4,976,722 A | 12/1990 | Failla |
| 4,988,355 A | 1/1991 | LeVeen et al. |
| 5,002,552 A | 3/1991 | Casey |
| 5,062,846 A | 11/1991 | Oh et al. |
| 5,094,753 A | 3/1992 | Allington et al. |
| 5,127,915 A | 7/1992 | Mattson |
| 5,132,014 A | 7/1992 | Allington et al. |
| 5,156,315 A | 10/1992 | Green et al. |
| 5,156,614 A | 10/1992 | Green et al. |
| 5,160,339 A | 11/1992 | Chen et al. |
| 5,160,624 A | 11/1992 | Clay et al. |
| 5,171,247 A | 12/1992 | Hughett et al. |
| 5,171,249 A | 12/1992 | Stefanchik et al. |
| 5,171,253 A | 12/1992 | Klieman |
| 5,173,188 A | 12/1992 | Winter et al. |
| 5,193,554 A | 3/1993 | McQuilkin |
| 5,198,197 A | 3/1993 | Clay et al. |
| 5,207,691 A | 5/1993 | Nardella |
| 5,246,456 A | 9/1993 | Wilkinson |
| 5,250,195 A | 10/1993 | Winter et al. |
| 5,253,793 A | 10/1993 | Green et al. |
| 5,257,999 A | 11/1993 | Slanetz, Jr. |
| 5,268,102 A | 12/1993 | Clay et al. |
| 5,268,103 A | 12/1993 | Jameson et al. |
| 5,269,930 A | 12/1993 | Jameson |
| 5,282,812 A | 2/1994 | Suarez, Jr. |
| 5,296,145 A | 3/1994 | Allington et al. |
| 5,306,234 A | 4/1994 | Johnson |
| 5,336,232 A | 8/1994 | Green et al. |
| 5,352,238 A | 10/1994 | Green et al. |
| 5,358,506 A | 10/1994 | Green et al. |
| 5,358,510 A | 10/1994 | Luscombe et al. |
| 5,366,458 A | 11/1994 | Korthoff et al. |
| 5,366,459 A | 11/1994 | Yoon |
| 5,368,600 A | 11/1994 | Failla et al. |
| 5,379,933 A | 1/1995 | Green et al. |
| 5,413,268 A | 5/1995 | Green et al. |
| 5,423,471 A | 6/1995 | Mastri et al. |
| 5,425,705 A | 6/1995 | Evard et al. |
| 5,425,740 A | 6/1995 | Hutchinson, Jr. |
| 5,441,507 A | 8/1995 | Wilk |
| 5,462,215 A | 10/1995 | Viola et al. |
| 5,462,558 A | 10/1995 | Kolesa et al. |
| 5,470,006 A | 11/1995 | Rodak |
| 5,470,009 A | 11/1995 | Rodak |
| 5,474,567 A | 12/1995 | Stefanchik et al. |
| 5,485,947 A | 1/1996 | Olson et al. |
| 5,490,856 A | 2/1996 | Person et al. |
| 5,501,693 A | 3/1996 | Gravener |
| 5,507,797 A | 4/1996 | Suzuki et al. |
| 5,509,920 A | 4/1996 | Phillips et al. |
| 5,531,744 A | 7/1996 | Nardella et al. |
| 5,547,117 A | 8/1996 | Hamblin et al. |
| 5,549,621 A | 8/1996 | Bessler et al. |
| 5,551,622 A | 9/1996 | Yoon |
| 5,554,169 A | 9/1996 | Green et al. |
| 5,560,530 A | 10/1996 | Bolanos et al. |
| 5,569,272 A | 10/1996 | Reed et al. |
| 5,573,169 A | 11/1996 | Green et al. |
| 5,575,802 A | 11/1996 | McQuilkin et al. |
| 5,580,067 A | 12/1996 | Hamblin et al. |
| 5,584,989 A | 12/1996 | Jameson |
| 5,591,178 A | 1/1997 | Green et al. |
| 5,597,107 A | 1/1997 | Knodel et al. |
| 5,601,573 A | 2/1997 | Fogelberg et al. |
| 5,601,707 A | 2/1997 | Clay et al. |
| 5,605,272 A | 2/1997 | Witt et al. |
| 5,605,273 A | 2/1997 | Hamblin et al. |
| 5,614,089 A | 3/1997 | Allington et al. |
| 5,620,452 A | 4/1997 | Yoon |
| 5,624,453 A | 4/1997 | Ahmed |
| 5,626,592 A | 5/1997 | Phillips et al. |
| 5,635,070 A | 6/1997 | Allington et al. |
| 5,643,291 A | 7/1997 | Pier et al. |
| 5,643,319 A | 7/1997 | Green et al. |
| 5,645,553 A | 7/1997 | Kolesa et al. |
| 5,653,373 A | 8/1997 | Green et al. |
| 5,653,885 A | 8/1997 | Jameson et al. |
| 5,655,698 A | 8/1997 | Yoon |
| 5,658,300 A | 8/1997 | Bito et al. |
| 5,662,259 A | 9/1997 | Yoon |
| 5,662,260 A | 9/1997 | Yoon |
| 5,665,085 A | 9/1997 | Nardella |
| 5,676,676 A | 10/1997 | Porter |
| 5,690,828 A | 11/1997 | Clay et al. |
| 5,695,502 A | 12/1997 | Pier et al. |
| 5,697,938 A | 12/1997 | Jensen et al. |
| 5,706,998 A | 1/1998 | Plyley et al. |
| 5,713,896 A | 2/1998 | Nardella |
| 5,713,912 A | 2/1998 | Porter |
| 5,715,987 A | 2/1998 | Kelley et al. |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,728,110 A | 3/1998 | Vidal et al. |
| 5,738,498 A | 4/1998 | Allington et al. |
| 5,741,283 A | 4/1998 | Fahy |
| 5,749,893 A | 5/1998 | Vidal et al. |
| 5,750,027 A | 5/1998 | Allington et al. |
| 5,755,559 A | 5/1998 | Allington et al. |
| 5,755,726 A | 5/1998 | Pratt et al. |
| 5,759,193 A | 6/1998 | Burbank et al. |
| 5,772,673 A | 6/1998 | Cuny et al. |
| 5,779,718 A | 7/1998 | Green et al. |
| 5,794,834 A | 8/1998 | Hamblin et al. |
| 5,797,932 A | 8/1998 | Min et al. |
| 5,833,695 A | 11/1998 | Yoon |
| 5,833,698 A | 11/1998 | Hinchliffe et al. |
| 5,833,700 A | 11/1998 | Fogelberg et al. |
| 5,843,101 A | 12/1998 | Fry |
| 5,846,255 A | 12/1998 | Casey |
| 5,849,019 A | 12/1998 | Yoon |
| 5,855,311 A | 1/1999 | Hamblin et al. |
| 5,865,791 A | 2/1999 | Whayne et al. |

(56) References Cited

U.S. PATENT DOCUMENTS

| | | |
|---|---|---|
| 5,868,761 A | 2/1999 | Nicholas et al. |
| 5,893,879 A | 4/1999 | Hirshowitz et al. |
| 5,911,881 A | 6/1999 | Clay et al. |
| 5,915,615 A | 6/1999 | Bauer |
| 5,921,997 A | 7/1999 | Fogelberg et al. |
| 5,932,095 A | 8/1999 | Walters et al. |
| 5,964,774 A | 10/1999 | McKean et al. |
| 5,972,022 A | 10/1999 | Huxel |
| 5,976,159 A | 11/1999 | Bolduc et al. |
| 6,015,417 A | 1/2000 | Reynolds, Jr. |
| 6,036,706 A | 3/2000 | Morejohn et al. |
| 6,042,599 A | 3/2000 | Huttner et al. |
| 6,051,003 A | 4/2000 | Chu et al. |
| 6,071,408 A | 6/2000 | Allington et al. |
| 6,083,399 A | 7/2000 | Jameson et al. |
| 6,086,767 A | 7/2000 | Walters et al. |
| 6,139,555 A | 10/2000 | Hart et al. |
| 6,149,814 A | 11/2000 | Allington et al. |
| 6,152,144 A | 11/2000 | Lesh et al. |
| 6,162,239 A | 12/2000 | Manhes |
| 6,206,897 B1 | 3/2001 | Jamiolkowski et al. |
| 6,231,561 B1 | 5/2001 | Frazier et al. |
| 6,238,414 B1 | 5/2001 | Griffiths |
| 6,241,890 B1 | 6/2001 | Clay et al. |
| 6,251,267 B1 | 6/2001 | Allington et al. |
| 6,273,897 B1 | 8/2001 | Dalessandro et al. |
| 6,280,407 B1 | 8/2001 | Manna et al. |
| 6,290,674 B1 | 9/2001 | Roue et al. |
| 6,294,088 B1 | 9/2001 | Allington et al. |
| 6,296,769 B1 | 10/2001 | Walters et al. |
| 6,319,410 B1 | 11/2001 | Allington et al. |
| 6,325,810 B1 | 12/2001 | Hamilton et al. |
| 6,328,727 B1 | 12/2001 | Frazier et al. |
| 6,332,864 B1 | 12/2001 | Schweich et al. |
| 6,338,710 B1 * | 1/2002 | Takahashi et al. .............. 600/37 |
| 6,379,366 B1 | 4/2002 | Fleischman et al. |
| 6,387,106 B1 | 5/2002 | Howell et al. |
| 6,391,038 B2 | 5/2002 | Vargas et al. |
| 6,406,485 B1 | 6/2002 | Hossain et al. |
| 6,419,669 B1 | 7/2002 | Frazier et al. |
| 6,419,682 B1 | 7/2002 | Appleby et al. |
| 6,421,920 B1 | 7/2002 | Jensen |
| RE37,814 E | 8/2002 | Allgeyer |
| 6,436,097 B1 | 8/2002 | Nardella |
| 6,436,108 B1 | 8/2002 | Mears |
| 6,458,100 B2 | 10/2002 | Roue et al. |
| 6,461,363 B1 | 10/2002 | Gadberry et al. |
| 6,461,368 B2 | 10/2002 | Fogarty et al. |
| 6,478,804 B2 | 11/2002 | Vargas et al. |
| 6,488,689 B1 | 12/2002 | Kaplan et al. |
| 6,503,259 B2 | 1/2003 | Huxel et al. |
| 6,508,829 B1 | 1/2003 | Levinson et al. |
| 6,517,556 B1 | 2/2003 | Monassevitch |
| 6,520,972 B2 | 2/2003 | Peters |
| 6,527,786 B1 | 3/2003 | Davis et al. |
| 6,551,303 B1 | 4/2003 | Van Tassel et al. |
| 6,558,408 B1 | 5/2003 | Fogarty et al. |
| 6,561,969 B2 | 5/2003 | Frazier et al. |
| 6,579,304 B1 | 6/2003 | Hart et al. |
| 6,582,451 B1 | 6/2003 | Marucci et al. |
| 6,592,600 B1 | 7/2003 | Nicolo |
| 6,629,988 B2 | 10/2003 | Weadock |
| 6,638,282 B2 | 10/2003 | Ramsey et al. |
| 6,641,557 B1 | 11/2003 | Frazier et al. |
| 6,644,618 B1 | 11/2003 | Balbo |
| 6,652,555 B1 | 11/2003 | VanTassel et al. |
| 6,652,556 B1 | 11/2003 | VanTassel et al. |
| 6,656,205 B1 | 12/2003 | Manhes |
| 6,663,653 B2 | 12/2003 | Akerfeldt |
| 6,685,715 B2 | 2/2004 | Danitz et al. |
| 6,689,150 B1 | 2/2004 | VanTassel et al. |
| 6,692,507 B2 | 2/2004 | Pugsley et al. |
| 6,699,258 B1 | 3/2004 | Sadler et al. |
| 6,702,825 B2 | 3/2004 | Frazier et al. |
| 6,702,826 B2 | 3/2004 | Liddicoat et al. |
| 6,712,804 B2 | 3/2004 | Roue et al. |
| 6,716,232 B1 | 4/2004 | Vidal et al. |
| 6,723,109 B2 | 4/2004 | Solingen |
| 6,730,108 B2 | 5/2004 | Van Tassel et al. |
| 6,746,461 B2 | 6/2004 | Fry |
| 6,746,472 B2 | 6/2004 | Frazier et al. |
| 6,755,338 B2 | 6/2004 | Hahnen et al. |
| 6,776,783 B1 | 8/2004 | Frantzen et al. |
| 6,776,785 B1 | 8/2004 | Yencho et al. |
| 6,780,195 B2 | 8/2004 | Porat |
| 6,790,172 B2 | 9/2004 | Alferness et al. |
| 6,817,972 B2 | 11/2004 | Snow |
| 6,821,285 B2 | 11/2004 | Laufer et al. |
| 6,830,174 B2 | 12/2004 | Hillstead et al. |
| 6,840,246 B2 | 1/2005 | Downing |
| 6,863,675 B2 | 3/2005 | Wilson, Jr. |
| 6,893,391 B2 | 5/2005 | Taylor |
| 6,916,332 B2 | 7/2005 | Adams |
| 6,926,712 B2 | 8/2005 | Phan |
| 6,949,113 B2 | 9/2005 | Van Tassel et al. |
| 6,974,462 B2 | 12/2005 | Sater |
| 6,994,092 B2 | 2/2006 | van der Burg et al. |
| 7,001,412 B2 | 2/2006 | Gallagher et al. |
| 7,033,378 B2 | 4/2006 | Smith et al. |
| 7,044,134 B2 | 5/2006 | Khairkhahan et al. |
| 7,070,083 B2 | 7/2006 | Jankowski |
| 7,077,856 B2 | 7/2006 | Whitman |
| 7,083,636 B2 | 8/2006 | Kortenbach |
| 7,108,703 B2 | 9/2006 | Danitz et al. |
| 7,128,073 B1 | 10/2006 | van der Burg et al. |
| 7,152,605 B2 | 12/2006 | Khairkhahan et al. |
| 7,220,272 B2 | 5/2007 | Weadock |
| 7,226,458 B2 | 6/2007 | Kaplan et al. |
| 7,285,131 B1 | 10/2007 | Bombard et al. |
| 7,300,444 B1 | 11/2007 | Nielsen et al. |
| 7,316,696 B2 | 1/2008 | Wilson et al. |
| 7,326,223 B2 | 2/2008 | Wilson, Jr. |
| 7,407,076 B2 | 8/2008 | Racenet et al. |
| 7,422,783 B2 | 9/2008 | Tremblay et al. |
| 7,427,279 B2 | 9/2008 | Frazier et al. |
| 7,438,208 B2 | 10/2008 | Larson |
| 7,438,718 B2 | 10/2008 | Milliman et al. |
| 7,473,258 B2 | 1/2009 | Clauson et al. |
| 7,473,261 B2 | 1/2009 | Rennich |
| 7,497,865 B2 | 3/2009 | Willis et al. |
| 7,503,474 B2 | 3/2009 | Hillstead et al. |
| 7,527,634 B2 | 5/2009 | Zenati et al. |
| 7,543,730 B1 | 6/2009 | Marczyk |
| 7,547,315 B2 | 6/2009 | Peterson et al. |
| 7,549,983 B2 | 6/2009 | Roue et al. |
| 7,553,315 B2 | 6/2009 | Kortenbach |
| 7,556,185 B2 | 7/2009 | Viola |
| 7,563,267 B2 | 7/2009 | Goldfarb et al. |
| 7,569,064 B1 | 8/2009 | Hausen et al. |
| 7,628,797 B2 | 12/2009 | Tieu et al. |
| 7,635,073 B2 | 12/2009 | Heinrich |
| 7,645,285 B2 | 1/2010 | Cosgrove et al. |
| 7,648,514 B1 | 1/2010 | Nakao |
| 7,658,311 B2 | 2/2010 | Boudreaux |
| 7,658,312 B2 | 2/2010 | Vidal et al. |
| 7,665,646 B2 | 2/2010 | Prommersberger |
| 7,673,782 B2 | 3/2010 | Hess et al. |
| 7,681,772 B2 | 3/2010 | Green et al. |
| 7,686,200 B2 | 3/2010 | Peterson |
| 7,686,759 B2 | 3/2010 | Sater |
| 7,686,820 B2 | 3/2010 | Huitema et al. |
| 7,699,860 B2 | 4/2010 | Huitema et al. |
| 7,713,276 B2 | 5/2010 | Dennis |
| 7,717,312 B2 | 5/2010 | Beetel |
| 7,717,937 B2 | 5/2010 | Wahr et al. |
| 7,722,527 B2 | 5/2010 | Bouchier et al. |
| 7,722,628 B2 | 5/2010 | Stokes et al. |
| 7,722,641 B2 | 5/2010 | van der Burg et al. |
| 7,722,643 B2 | 5/2010 | Schaller et al. |
| 7,727,142 B2 | 6/2010 | Hjelle et al. |
| 7,727,189 B2 | 6/2010 | VanTassel et al. |
| 7,731,073 B2 | 6/2010 | Wixey et al. |
| 7,735,493 B2 | 6/2010 | van der Burg et al. |
| 7,735,703 B2 | 6/2010 | Morgan et al. |

(56) References Cited

U.S. PATENT DOCUMENTS

| | | |
|---|---|---|
| 7,740,159 B2 | 6/2010 | Shelton et al. |
| 7,749,249 B2 | 7/2010 | Gelbart et al. |
| 7,753,245 B2 | 7/2010 | Boudreaux et al. |
| 7,753,248 B2 | 7/2010 | Viola |
| 7,757,924 B2 | 7/2010 | Gerbi et al. |
| 7,758,610 B2 | 7/2010 | Kanner et al. |
| 7,766,207 B2 | 8/2010 | Mather et al. |
| 7,766,924 B1 | 8/2010 | Bombard et al. |
| 7,770,774 B2 | 8/2010 | Mastri et al. |
| 7,780,683 B2 | 8/2010 | Roue et al. |
| 7,780,685 B2 | 8/2010 | Hunt et al. |
| 7,794,475 B2 | 9/2010 | Hess et al. |
| 7,819,886 B2 | 10/2010 | Whitfield et al. |
| 7,828,188 B2 | 11/2010 | Jankowski |
| 7,828,810 B2 | 11/2010 | Liddicoat et al. |
| 7,845,533 B2 | 12/2010 | Marczyk et al. |
| 7,846,168 B2 | 12/2010 | Liddicoat et al. |
| 7,862,571 B2 | 1/2011 | Dennis |
| 7,866,523 B1 | 1/2011 | White et al. |
| 7,891,534 B2 | 2/2011 | Wenchell et al. |
| 7,892,244 B2 | 2/2011 | Monassevitch et al. |
| 7,896,895 B2 | 3/2011 | Boudreaux et al. |
| 7,896,896 B2 | 3/2011 | Viola |
| 7,909,224 B2 | 3/2011 | Prommersberger |
| 7,913,893 B2 | 3/2011 | Mastri et al. |
| 7,926,691 B2 | 4/2011 | Viola et al. |
| 7,931,578 B2 | 4/2011 | Whayne et al. |
| 7,950,561 B2 | 5/2011 | Aranyi |
| 7,951,069 B2 | 5/2011 | Bertolero |
| 7,951,147 B2 | 5/2011 | Privitera et al. |
| 7,954,686 B2 | 6/2011 | Baxter et al. |
| 7,959,555 B2 | 6/2011 | Dietz et al. |
| 7,967,178 B2 | 6/2011 | Scirica et al. |
| 7,967,180 B2 | 6/2011 | Scirica |
| 7,992,757 B2 | 8/2011 | Wheeler et al. |
| 8,002,795 B2 | 8/2011 | Beetel |
| 8,007,504 B2 | 8/2011 | Zenati et al. |
| 8,011,553 B2 | 9/2011 | Mastri et al. |
| 8,016,177 B2 | 9/2011 | Bettuchi et al. |
| 8,021,378 B2 | 9/2011 | Sixto et al. |
| 8,028,884 B2 | 10/2011 | Sniffin et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,066,168 B2 | 11/2011 | Vidal et al. |
| 8,066,721 B2 | 11/2011 | Kortenbach et al. |
| 8,070,033 B2 | 12/2011 | Milliman et al. |
| 8,070,035 B2 | 12/2011 | Holsten et al. |
| 8,070,038 B2 | 12/2011 | Kostrzewski |
| 8,074,861 B2 | 12/2011 | Ehrenfels et al. |
| 8,074,862 B2 | 12/2011 | Shah |
| 8,080,020 B2 | 12/2011 | Kortenbach et al. |
| 8,080,032 B2 | 12/2011 | van der Burg et al. |
| 8,083,118 B2 | 12/2011 | Milliman et al. |
| 8,083,119 B2 | 12/2011 | Prommersberger |
| 8,091,753 B2 | 1/2012 | Viola |
| 8,091,756 B2 | 1/2012 | Viola |
| 8,096,459 B2 | 1/2012 | Ortiz et al. |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,114,123 B2 | 2/2012 | Brenzel et al. |
| 8,118,207 B2 | 2/2012 | Racenet et al. |
| 8,123,101 B2 | 2/2012 | Racenet et al. |
| 8,128,642 B2 | 3/2012 | Heeps et al. |
| 8,152,041 B2 | 4/2012 | Kostrzewski |
| 8,152,823 B2 | 4/2012 | Kassab et al. |
| 8,157,149 B2 | 4/2012 | Olson et al. |
| 8,157,152 B2 | 4/2012 | Holsten et al. |
| 8,162,197 B2 | 4/2012 | Mastri et al. |
| 8,172,122 B2 | 5/2012 | Kasvikis et al. |
| 8,181,837 B2 | 5/2012 | Roy |
| 8,186,558 B2 | 5/2012 | Sapienza |
| 8,187,286 B2 | 5/2012 | Jugenheimer et al. |
| 8,191,752 B2 | 6/2012 | Scirica |
| 8,192,460 B2 | 6/2012 | Orban et al. |
| 8,196,796 B2 | 6/2012 | Shelton et al. |
| 8,205,620 B2 | 6/2012 | Taylor et al. |
| 8,205,780 B2 | 6/2012 | Sorrentino et al. |
| 8,205,781 B2 | 6/2012 | Baxter et al. |
| 8,210,412 B2 | 7/2012 | Marczyk |
| 8,210,413 B2 | 7/2012 | Whitman et al. |
| 8,210,414 B2 | 7/2012 | Bettuchi et al. |
| 8,210,416 B2 | 7/2012 | Milliman et al. |
| 8,215,532 B2 | 7/2012 | Marczyk |
| 8,220,690 B2 | 7/2012 | Hess et al. |
| 8,221,445 B2 | 7/2012 | van Tassel et al. |
| 8,225,980 B1 | 7/2012 | Rivera |
| 8,231,040 B2 | 7/2012 | Zemlok et al. |
| 8,235,272 B2 | 8/2012 | Nicholas et al. |
| 8,235,274 B2 | 8/2012 | Cappola |
| 8,236,015 B2 | 8/2012 | Bettuchi et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,900 B2 | 8/2012 | Scirica |
| 8,245,901 B2 | 8/2012 | Stopek |
| 8,246,634 B2 | 8/2012 | Huitema et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,849 B2 | 9/2012 | Wazer et al. |
| 8,272,552 B2 | 9/2012 | Holsten et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,800 B2 | 10/2012 | Bettuchi |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,281,975 B2 | 10/2012 | Criscuolo et al. |
| 8,286,847 B2 | 10/2012 | Taylor |
| 8,286,848 B2 | 10/2012 | Wenchell et al. |
| 8,287,563 B2 | 10/2012 | Khairkhahan et al. |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton et al. |
| 8,292,156 B2 | 10/2012 | Kostrzewski |
| 8,292,158 B2 | 10/2012 | Sapienza |
| 8,403,197 B2 | 3/2013 | Vidal et al. |
| 8,561,872 B2 * | 10/2013 | Wheeler et al. ............ 227/176.1 |
| 8,685,055 B2 | 4/2014 | VanTassel et al. |
| 2001/0005787 A1 | 6/2001 | Oz et al. |
| 2001/0014811 A1 | 8/2001 | Hussein |
| 2001/0016748 A1 | 8/2001 | Tanner et al. |
| 2001/0034536 A1 | 10/2001 | Looper et al. |
| 2001/0039423 A1 | 11/2001 | Skiba et al. |
| 2001/0041914 A1 | 11/2001 | Frazier et al. |
| 2002/0022880 A1 | 2/2002 | Melvin |
| 2002/0032454 A1 | 3/2002 | Durgin et al. |
| 2002/0049457 A1 | 4/2002 | Kaplan et al. |
| 2002/0055750 A1 | 5/2002 | Durgin et al. |
| 2002/0065535 A1 | 5/2002 | Kneifel et al. |
| 2002/0068945 A1 | 6/2002 | Sixto et al. |
| 2002/0072759 A1 | 6/2002 | Fry |
| 2002/0082621 A1 | 6/2002 | Schurr et al. |
| 2002/0103492 A1 | 8/2002 | Kaplan et al. |
| 2002/0111637 A1 | 8/2002 | Kaplan et al. |
| 2002/0120281 A1 | 8/2002 | Overaker |
| 2002/0138086 A1 | 9/2002 | Sixto et al. |
| 2002/0151889 A1 | 10/2002 | Swanson et al. |
| 2002/0173848 A1 | 11/2002 | Sachs |
| 2002/0177863 A1 | 11/2002 | Mandel et al. |
| 2002/0183770 A1 | 12/2002 | Anderson |
| 2002/0183771 A1 | 12/2002 | Burbank et al. |

(56) References Cited

U.S. PATENT DOCUMENTS

| | | |
|---|---|---|
| 2002/0183785 A1 | 12/2002 | Howell et al. |
| 2002/0198549 A1 | 12/2002 | Sixto et al. |
| 2003/0065340 A1 | 4/2003 | Geitz |
| 2003/0078603 A1 | 4/2003 | Schaller et al. |
| 2003/0114865 A1 | 6/2003 | Sater |
| 2003/0120337 A1 | 6/2003 | Van Tassel et al. |
| 2003/0125729 A1 | 7/2003 | Hooven et al. |
| 2003/0125755 A1 | 7/2003 | Schaller et al. |
| 2003/0130670 A1 | 7/2003 | Anderson et al. |
| 2003/0153930 A1 | 8/2003 | De Canniere |
| 2003/0158464 A1 | 8/2003 | Bertolero |
| 2003/0158604 A1 | 8/2003 | Cauthen et al. |
| 2003/0181929 A1 | 9/2003 | Geitz |
| 2003/0191479 A1 | 10/2003 | Thornton |
| 2003/0191494 A1 | 10/2003 | Gray et al. |
| 2003/0191526 A1 | 10/2003 | Van Tassel et al. |
| 2003/0195531 A1 | 10/2003 | Gardiner et al. |
| 2003/0216757 A1 | 11/2003 | Gerberding |
| 2003/0220660 A1 | 11/2003 | Kortenbach et al. |
| 2003/0220667 A1 | 11/2003 | van der Burg et al. |
| 2003/0225421 A1 | 12/2003 | Peavey et al. |
| 2003/0225423 A1 | 12/2003 | Huitema |
| 2003/0225424 A1 | 12/2003 | Benderev |
| 2003/0229367 A1 | 12/2003 | Viola |
| 2003/0233095 A1 | 12/2003 | Urbanski et al. |
| 2003/0236537 A1 | 12/2003 | Hart et al. |
| 2004/0006353 A1 | 1/2004 | Bosley et al. |
| 2004/0024414 A1 | 2/2004 | Downing |
| 2004/0030335 A1 | 2/2004 | Zenati et al. |
| 2004/0034375 A1 | 2/2004 | Ruiz et al. |
| 2004/0049210 A1 | 3/2004 | VanTassel et al. |
| 2004/0059354 A1 | 3/2004 | Smith et al. |
| 2004/0059359 A1 | 3/2004 | Wilson |
| 2004/0073234 A1 | 4/2004 | Chu et al. |
| 2004/0073241 A1 | 4/2004 | Barry et al. |
| 2004/0089312 A1 | 5/2004 | Jordan |
| 2004/0092973 A1 | 5/2004 | Chanduszko et al. |
| 2004/0093024 A1 | 5/2004 | Lousararian et al. |
| 2004/0097980 A1 | 5/2004 | Ferree |
| 2004/0097982 A1 | 5/2004 | Jugenheimer et al. |
| 2004/0111100 A1 | 6/2004 | Benderev et al. |
| 2004/0116948 A1 | 6/2004 | Sixto et al. |
| 2004/0122456 A1 | 6/2004 | Saadat et al. |
| 2004/0122467 A1 | 6/2004 | VanTassel et al. |
| 2004/0127919 A1 | 7/2004 | Trout et al. |
| 2004/0127935 A1 | 7/2004 | VanTassel et al. |
| 2004/0133214 A1 | 7/2004 | Kayan |
| 2004/0133215 A1 | 7/2004 | Baxter |
| 2004/0133219 A1 | 7/2004 | Forsell |
| 2004/0138683 A1 | 7/2004 | Shelton et al. |
| 2004/0186486 A1 | 9/2004 | Roue et al. |
| 2004/0193188 A1 | 9/2004 | Francese |
| 2004/0199178 A1 | 10/2004 | Small |
| 2004/0230222 A1 | 11/2004 | van der Burg et al. |
| 2005/0004652 A1 | 1/2005 | van der Burg et al. |
| 2005/0021061 A1 | 1/2005 | Dennis |
| 2005/0021062 A1 | 1/2005 | Dennis |
| 2005/0027308 A1 | 2/2005 | Davis et al. |
| 2005/0049573 A1 | 3/2005 | Van Tassel et al. |
| 2005/0059988 A1 | 3/2005 | Danitz et al. |
| 2005/0125010 A1 | 6/2005 | Smith et al. |
| 2005/0143767 A1 | 6/2005 | Kimura et al. |
| 2005/0146069 A1 | 7/2005 | Kanan |
| 2005/0149068 A1 | 7/2005 | Williams et al. |
| 2005/0149069 A1 | 7/2005 | Bertolero et al. |
| 2005/0149988 A1 | 7/2005 | Grannan |
| 2005/0149989 A1 | 7/2005 | Lupoi et al. |
| 2005/0154404 A1 | 7/2005 | Liddicoat et al. |
| 2005/0165421 A1 | 7/2005 | Wilson et al. |
| 2005/0165422 A1 | 7/2005 | Wilson |
| 2005/0165423 A1 | 7/2005 | Gallagher et al. |
| 2005/0165424 A1 | 7/2005 | Gallagher et al. |
| 2005/0171560 A1 | 8/2005 | Hughett |
| 2005/0177180 A1 | 8/2005 | Kaganov et al. |
| 2005/0177182 A1 | 8/2005 | van der Burg et al. |
| 2005/0177224 A1 | 8/2005 | Fogarty et al. |
| 2005/0177232 A1 | 8/2005 | Ashton |
| 2005/0187569 A1 | 8/2005 | Dahl et al. |
| 2005/0251184 A1 | 11/2005 | Anderson |
| 2005/0273122 A1 | 12/2005 | Theroux et al. |
| 2005/0277955 A1 | 12/2005 | Palmer et al. |
| 2005/0277959 A1 | 12/2005 | Cosgrove et al. |
| 2006/0004388 A1 | 1/2006 | Whayne et al. |
| 2006/0004390 A1 | 1/2006 | Rosenberg et al. |
| 2006/0020162 A1 | 1/2006 | Whayne et al. |
| 2006/0020271 A1 | 1/2006 | Stewart et al. |
| 2006/0020275 A1 | 1/2006 | Goldfarb et al. |
| 2006/0100644 A1 | 5/2006 | Viola |
| 2006/0100649 A1 | 5/2006 | Hart |
| 2006/0111735 A1 | 5/2006 | Crainich |
| 2006/0217749 A1 | 9/2006 | Wilson et al. |
| 2006/0264979 A1 | 11/2006 | Shepard |
| 2006/0264987 A1 | 11/2006 | Sgro |
| 2007/0005108 A1 | 1/2007 | Simhon et al. |
| 2007/0016228 A1 | 1/2007 | Salas |
| 2007/0060951 A1 | 3/2007 | Shannon |
| 2007/0073274 A1 | 3/2007 | Chin et al. |
| 2007/0083218 A1 | 4/2007 | A. Morris |
| 2007/0083227 A1 | 4/2007 | van der Burg et al. |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0135826 A1 | 6/2007 | Zaver et al. |
| 2007/0149988 A1 | 6/2007 | Michler et al. |
| 2007/0149989 A1 | 6/2007 | Santilli et al. |
| 2007/0149995 A1 | 6/2007 | Quinn et al. |
| 2007/0162060 A1 | 7/2007 | Wild |
| 2007/0167964 A1 | 7/2007 | Willis |
| 2007/0179512 A1 | 8/2007 | Olsen et al. |
| 2007/0185506 A1 | 8/2007 | Jackson |
| 2007/0191868 A1 | 8/2007 | Theroux et al. |
| 2007/0203391 A1 | 8/2007 | Bloom et al. |
| 2007/0208357 A1 | 9/2007 | Houser et al. |
| 2007/0213747 A1 | 9/2007 | Monassevitch et al. |
| 2007/0246505 A1 | 10/2007 | Pace-Floridia et al. |
| 2007/0250086 A1 | 10/2007 | Wiley et al. |
| 2007/0260278 A1 | 11/2007 | Wheeler et al. |
| 2007/0265640 A1 | 11/2007 | Kortenbach et al. |
| 2007/0265641 A1 | 11/2007 | Roue et al. |
| 2007/0265642 A1 | 11/2007 | Chanduszko et al. |
| 2007/0270891 A1 | 11/2007 | McGuckin |
| 2007/0276417 A1 | 11/2007 | Mendes Jr. et al. |
| 2008/0009866 A1 | 1/2008 | Alamin et al. |
| 2008/0021466 A1 | 1/2008 | Shadduck et al. |
| 2008/0021484 A1 | 1/2008 | Catanese et al. |
| 2008/0027471 A1 | 1/2008 | Hauri |
| 2008/0027478 A1 | 1/2008 | Connors et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0039922 A1 | 2/2008 | Miles et al. |
| 2008/0060658 A1 | 3/2008 | Doorschodt |
| 2008/0071294 A1 | 3/2008 | Bender et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0097571 A1 | 4/2008 | Denison et al. |
| 2008/0105265 A1 | 5/2008 | Pannell et al. |
| 2008/0125795 A1 | 5/2008 | Kaplan et al. |
| 2008/0125796 A1 | 5/2008 | Graham |
| 2008/0132891 A1 | 6/2008 | Nobis et al. |
| 2008/0147083 A1 | 6/2008 | Vold et al. |
| 2008/0177292 A1 | 7/2008 | Jacobs et al. |
| 2008/0183283 A1 | 7/2008 | Downing |
| 2008/0208324 A1 | 8/2008 | Glithero et al. |
| 2008/0215090 A1 | 9/2008 | Gonzales et al. |
| 2008/0234785 A1 | 9/2008 | Nakayama et al. |
| 2008/0249547 A1 | 10/2008 | Dunn |
| 2008/0269787 A1 | 10/2008 | Laufer |
| 2008/0287989 A1 | 11/2008 | Weisel et al. |

(56) References Cited

U.S. PATENT DOCUMENTS

| | | |
|---|---|---|
| 2008/0294179 A1 | 11/2008 | Balbierz et al. |
| 2008/0300686 A1 | 12/2008 | Khoo |
| 2008/0312670 A1 | 12/2008 | Lutze et al. |
| 2008/0319456 A1 | 12/2008 | Hart |
| 2009/0001121 A1 | 1/2009 | Hess et al. |
| 2009/0001124 A1 | 1/2009 | Hess et al. |
| 2009/0005808 A1 | 1/2009 | Hess et al. |
| 2009/0012545 A1 | 1/2009 | Williamson et al. |
| 2009/0020584 A1 | 1/2009 | Soltz et al. |
| 2009/0048665 A1 | 2/2009 | Miron et al. |
| 2009/0054916 A1 | 2/2009 | Meier et al. |
| 2009/0088783 A1 | 4/2009 | Kennedy et al. |
| 2009/0093826 A1 | 4/2009 | Warder-Gabaldon |
| 2009/0105731 A1 | 4/2009 | Priewe |
| 2009/0112249 A1 | 4/2009 | Miles et al. |
| 2009/0118748 A1 | 5/2009 | Pugsley et al. |
| 2009/0131959 A1 | 5/2009 | Rolland |
| 2009/0138028 A1 | 5/2009 | Wells et al. |
| 2009/0163937 A1 | 6/2009 | Kassab et al. |
| 2009/0171380 A1 | 7/2009 | Whiting |
| 2009/0171386 A1 | 7/2009 | Amplatz et al. |
| 2009/0177212 A1 | 7/2009 | Carley et al. |
| 2009/0182326 A1 | 7/2009 | Zenati et al. |
| 2009/0182374 A1 | 7/2009 | Keith |
| 2009/0182419 A1 | 7/2009 | Bolling |
| 2009/0187198 A1 | 7/2009 | Weitzner |
| 2009/0206127 A1 | 8/2009 | Danielson et al. |
| 2009/0209986 A1 | 8/2009 | Stewart et al. |
| 2009/0222025 A1 | 9/2009 | Catanese et al. |
| 2009/0240267 A1 | 9/2009 | Crawley et al. |
| 2009/0240268 A1 | 9/2009 | Kassab et al. |
| 2009/0264880 A1 | 10/2009 | Solem |
| 2009/0277948 A1 | 11/2009 | Beardsley et al. |
| 2010/0023023 A1 | 1/2010 | Popovic et al. |
| 2010/0063541 A1 | 3/2010 | Brunelle et al. |
| 2010/0069924 A1 | 3/2010 | Kochman et al. |
| 2010/0069928 A1 | 3/2010 | Bauer |
| 2010/0069930 A1 | 3/2010 | Roslin et al. |
| 2010/0082047 A1 | 4/2010 | Cosgrove et al. |
| 2010/0114124 A1 | 5/2010 | Kelleher et al. |
| 2010/0114133 A1 | 5/2010 | Huitema et al. |
| 2010/0114134 A1 | 5/2010 | McIntyre |
| 2010/0114157 A1 | 5/2010 | Sabanathan et al. |
| 2010/0115739 A1 | 5/2010 | Mathur |
| 2010/0121359 A1 | 5/2010 | Atui |
| 2010/0125288 A1 | 5/2010 | Gelfand et al. |
| 2010/0130965 A1 | 5/2010 | Sibbitt et al. |
| 2010/0137885 A1 | 6/2010 | Ortiz et al. |
| 2010/0145361 A1 | 6/2010 | Francischelli et al. |
| 2010/0155453 A1 | 6/2010 | Bombard et al. |
| 2010/0163054 A1 | 7/2010 | Breznel et al. |
| 2010/0168791 A1 | 7/2010 | Kassab et al. |
| 2010/0179570 A1 | 7/2010 | Privitera et al. |
| 2010/0185219 A1 | 7/2010 | Gertzman et al. |
| 2010/0185221 A1 | 7/2010 | Shipp |
| 2010/0186750 A1 | 7/2010 | Tran et al. |
| 2010/0191279 A1 | 7/2010 | Kassab et al. |
| 2010/0204716 A1 | 8/2010 | Stewart et al. |
| 2010/0211046 A1 | 8/2010 | Adams et al. |
| 2010/0217314 A1 | 8/2010 | Holsten et al. |
| 2010/0222789 A1 | 9/2010 | Gelbart et al. |
| 2010/0228269 A1 | 9/2010 | Garrison et al. |
| 2010/0228279 A1 | 9/2010 | Miles et al. |
| 2010/0228285 A1 | 9/2010 | Miles et al. |
| 2010/0234862 A1 | 9/2010 | Patel et al. |
| 2010/0241139 A1 | 9/2010 | Harshman |
| 2010/0256660 A1 | 10/2010 | Anderson |
| 2010/0286718 A1 | 11/2010 | Kassab et al. |
| 2010/0292719 A1 | 11/2010 | Ducharme |
| 2010/0324572 A1 | 12/2010 | Needleman et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2010/0331862 A1 | 12/2010 | Monassevitch et al. |
| 2011/0009853 A1 | 1/2011 | Bertolero et al. |
| 2011/0022079 A1 | 1/2011 | Miles et al. |
| 2011/0036896 A1 | 2/2011 | Buessler et al. |
| 2011/0046437 A1 | 2/2011 | Kassab et al. |
| 2011/0046641 A1 | 2/2011 | Kassab et al. |
| 2011/0054515 A1 | 3/2011 | Bridgeman et al. |
| 2011/0068143 A1 | 3/2011 | Laufer et al. |
| 2011/0071547 A1 | 3/2011 | McBrayer et al. |
| 2011/0071555 A1 | 3/2011 | McBrayer et al. |
| 2011/0082495 A1 | 4/2011 | Ruiz |
| 2011/0112559 A1 | 5/2011 | Monassevitch et al. |
| 2011/0125171 A1 | 5/2011 | Viola |
| 2011/0144661 A1 | 6/2011 | Houser et al. |
| 2011/0152895 A1 | 6/2011 | Nyuli et al. |
| 2011/0155788 A1 | 6/2011 | Hillstead et al. |
| 2011/0174863 A1 | 7/2011 | Shelton et al. |
| 2011/0178534 A1 | 7/2011 | Whitman et al. |
| 2011/0178535 A1 | 7/2011 | Whitman |
| 2011/0178539 A1 | 7/2011 | Holmes et al. |
| 2011/0190791 A1 | 8/2011 | Jacobs et al. |
| 2011/0190809 A1 | 8/2011 | Mohan et al. |
| 2011/0208233 A1 | 8/2011 | McGuckin et al. |
| 2011/0218566 A1 | 9/2011 | van der Burg et al. |
| 2011/0224700 A1 | 9/2011 | Schmidt et al. |
| 2011/0224701 A1 | 9/2011 | Menn |
| 2011/0230903 A1 | 9/2011 | Bertolero |
| 2011/0238094 A1 | 9/2011 | Thomas et al. |
| 2011/0245849 A1 | 10/2011 | Jabba et al. |
| 2011/0270285 A1 | 11/2011 | Lissa |
| 2011/0270303 A1 | 11/2011 | Wheeler et al. |
| 2011/0295290 A1 | 12/2011 | Whitfield |
| 2011/0295291 A1 | 12/2011 | Trivisani |
| 2011/0313437 A1 | 12/2011 | Yeh |
| 2012/0010635 A1 | 1/2012 | Yeretsian |
| 2012/0035631 A1 | 2/2012 | Hughett et al. |
| 2012/0035643 A1 | 2/2012 | Khairkhahan et al. |
| 2012/0059400 A1 | 3/2012 | Williamson et al. |
| 2012/0065662 A1 | 3/2012 | van der Burg et al. |
| 2012/0065667 A1 | 3/2012 | Javois et al. |
| 2012/0071918 A1 | 3/2012 | Amin et al. |
| 2012/0074198 A1 | 3/2012 | Huitema et al. |
| 2012/0080478 A1 | 4/2012 | Morgan et al. |
| 2012/0080479 A1 | 4/2012 | Shelton, IV |
| 2012/0080480 A1 | 4/2012 | Woodard et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard et al. |
| 2012/0080486 A1 | 4/2012 | Woodard et al. |
| 2012/0080487 A1 | 4/2012 | Woodard et al. |
| 2012/0080488 A1 | 4/2012 | Shelton et al. |
| 2012/0080489 A1 | 4/2012 | Shelton et al. |
| 2012/0080490 A1 | 4/2012 | Shelton et al. |
| 2012/0080491 A1 | 4/2012 | Shelton et al. |
| 2012/0080503 A1 | 4/2012 | Woodard et al. |
| 2012/0083803 A1 | 4/2012 | Patel et al. |
| 2012/0093903 A1 | 4/2012 | Roth et al. |
| 2012/0101509 A1 | 4/2012 | Paganon |
| 2012/0109161 A1 | 5/2012 | Privitera et al. |
| 2012/0111920 A1 | 5/2012 | Kostrzewski |
| 2012/0123445 A1 | 5/2012 | Hughett et al. |
| 2012/0130402 A1 | 5/2012 | Heeps et al. |
| 2012/0130421 A1 | 5/2012 | Hafez et al. |
| 2012/0145767 A1 | 6/2012 | Shah et al. |
| 2012/0145768 A1 | 6/2012 | Sorrentino et al. |
| 2012/0158022 A1 | 6/2012 | Kaplan et al. |
| 2012/0160890 A1 | 6/2012 | Holcomb et al. |
| 2012/0172927 A1 | 7/2012 | Campbell et al. |
| 2012/0209297 A1 | 8/2012 | Jugenheimer et al. |
| 2012/0228359 A1 | 9/2012 | Viola |
| 2012/0239083 A1 | 9/2012 | Kreidler |
| 2012/0241503 A1 | 9/2012 | Baxter et al. |
| 2012/0241505 A1 | 9/2012 | Alexander et al. |
| 2012/0245605 A1 | 9/2012 | Nicholson, IV |
| 2012/0248169 A1 | 10/2012 | Widenhouse et al. |
| 2012/0271337 A1 | 10/2012 | Figulla et al. |

(56) References Cited

U.S. PATENT DOCUMENTS

| | | |
|---|---|---|
| 2012/0283585 A1 | 11/2012 | Werneth et al. |
| 2012/0283773 A1 | 11/2012 | Van Tassel et al. |
| 2014/0163605 A1 | 6/2014 | VanTassel et al. |

FOREIGN PATENT DOCUMENTS

| | | |
|---|---|---|
| DE | 19534320 C1 | 2/1997 |
| DE | 19537299 A1 | 4/1997 |
| DE | 19707382 A1 | 9/1997 |
| DE | 29716753 U1 | 12/1997 |
| DE | 29715758 U1 | 2/1998 |
| DE | 19738306 A1 | 3/1999 |
| DE | 19741053 A1 | 4/1999 |
| DE | 29822558 U1 | 4/1999 |
| DE | 29913246 U1 | 10/1999 |
| DE | 19925304 A1 | 12/1999 |
| DE | 19832739 A1 | 2/2000 |
| DE | 19860685 A1 | 7/2000 |
| DE | 19858577 C1 | 9/2000 |
| DE | 19951940 A1 | 6/2001 |
| DE | 10212385 A1 | 11/2002 |
| DE | 20214068 U1 | 12/2002 |
| DE | 20208744 U1 | 2/2003 |
| DE | 10203946 A1 | 3/2003 |
| DE | 10347391 A1 | 5/2005 |
| DE | 102004015223 A1 | 10/2005 |
| DE | 102004026617 A1 | 12/2005 |
| DE | 202007003398 U1 | 7/2007 |
| DE | 102009018819 A1 | 10/2010 |
| DE | 102009018821 A1 | 10/2010 |
| DE | 202010008941 U1 | 1/2011 |
| DE | 102010060322 A1 | 5/2012 |
| DE | 202012001672 U1 | 5/2012 |
| EP | 0138687 A1 | 4/1985 |
| EP | 138687 A1 | 4/1985 |
| EP | 169044 A2 | 1/1986 |
| EP | 314064 A2 | 5/1989 |
| EP | 324549 A2 | 7/1989 |
| EP | 476523 A2 | 3/1992 |
| EP | 489436 A1 | 6/1992 |
| EP | 490411 A1 | 6/1992 |
| EP | 492283 A1 | 7/1992 |
| EP | 510826 A1 | 10/1992 |
| EP | 537572 A2 | 4/1993 |
| EP | 567965 A2 | 11/1993 |
| EP | 576835 A2 | 1/1994 |
| EP | 578425 A1 | 1/1994 |
| EP | 594002 A1 | 4/1994 |
| EP | 594004 A1 | 4/1994 |
| EP | 598976 A2 | 6/1994 |
| EP | 600182 A2 | 6/1994 |
| EP | 609612 A2 | 8/1994 |
| EP | 610307 A1 | 8/1994 |
| EP | 674876 A2 | 10/1995 |
| EP | 676173 A1 | 10/1995 |
| EP | 681810 A2 | 11/1995 |
| EP | 696179 A1 | 2/1996 |
| EP | 699415 A2 | 3/1996 |
| EP | 704190 A1 | 4/1996 |
| EP | 714633 A1 | 6/1996 |
| EP | 724405 A1 | 8/1996 |
| EP | 754433 A2 | 1/1997 |
| EP | 758214 A1 | 2/1997 |
| EP | 763346 A1 | 3/1997 |
| EP | 763347 A1 | 3/1997 |
| EP | 780107 A1 | 6/1997 |
| EP | 790804 A1 | 8/1997 |
| EP | 793944 A1 | 9/1997 |
| EP | 885595 A1 | 12/1998 |
| EP | 893970 A1 | 2/1999 |
| EP | 897696 A1 | 2/1999 |
| EP | 910293 A1 | 4/1999 |
| EP | 981296 A1 | 3/2000 |
| EP | 1072225 A2 | 1/2001 |
| EP | 1090592 A1 | 4/2001 |
| EP | 1100382 A1 | 5/2001 |
| EP | 1465532 B1 | 7/2001 |
| EP | 1199990 A1 | 5/2002 |
| EP | 1233708 A2 | 8/2002 |
| EP | 1250096 A2 | 10/2002 |
| EP | 1254636 A2 | 11/2002 |
| EP | 1256317 A2 | 11/2002 |
| EP | 1289428 A2 | 3/2003 |
| EP | 1289432 A1 | 3/2003 |
| EP | 1326544 A1 | 7/2003 |
| EP | 1339327 A2 | 9/2003 |
| EP | 1342451 A1 | 9/2003 |
| EP | 1462061 A2 | 9/2004 |
| EP | 1462062 A2 | 9/2004 |
| EP | 1389065 B1 | 4/2005 |
| EP | 1600108 A2 | 11/2005 |
| EP | 1694218 A2 | 8/2006 |
| EP | 1709915 A1 | 10/2006 |
| EP | 1437972 B1 | 11/2006 |
| EP | 1418848 B1 | 2/2007 |
| EP | 1757235 A1 | 2/2007 |
| EP | 1767157 A1 | 3/2007 |
| EP | 1774914 A1 | 4/2007 |
| EP | 1774915 A1 | 4/2007 |
| EP | 1810622 A1 | 7/2007 |
| EP | 1545332 B1 | 8/2007 |
| EP | 1813214 A1 | 8/2007 |
| EP | 1815803 A1 | 8/2007 |
| EP | 1829489 A1 | 9/2007 |
| EP | 1852141 A2 | 11/2007 |
| EP | 1455653 B1 | 4/2008 |
| EP | 1908412 A2 | 4/2008 |
| EP | 1908413 A1 | 4/2008 |
| EP | 1908415 A1 | 4/2008 |
| EP | 1913881 A1 | 4/2008 |
| EP | 1949863 A1 | 7/2008 |
| EP | 1980214 A2 | 10/2008 |
| EP | 1603465 B1 | 2/2009 |
| EP | 2044892 A2 | 4/2009 |
| EP | 1357843 B1 | 5/2009 |
| EP | 2074954 A1 | 7/2009 |
| EP | 2098170 A2 | 9/2009 |
| EP | 2098175 A1 | 9/2009 |
| EP | 2110082 A1 | 10/2009 |
| EP | 2110083 A2 | 10/2009 |
| EP | 2110084 A2 | 10/2009 |
| EP | 2113209 A1 | 11/2009 |
| EP | 2116193 A1 | 11/2009 |
| EP | 2116194 A2 | 11/2009 |
| EP | 2116195 A1 | 11/2009 |
| EP | 1545333 B1 | 12/2009 |
| EP | 2130501 A1 | 12/2009 |
| EP | 2151204 A1 | 2/2010 |
| EP | 1874196 B1 | 3/2010 |
| EP | 2158854 A1 | 3/2010 |
| EP | 1492460 B1 | 6/2010 |
| EP | 2241265 A1 | 10/2010 |
| EP | 2253279 A1 | 11/2010 |
| EP | 2286737 A1 | 2/2011 |
| EP | 1971276 B1 | 4/2011 |
| EP | 2316351 A2 | 5/2011 |
| EP | 2328482 A1 | 6/2011 |
| EP | 2347722 A1 | 7/2011 |
| EP | 1993451 B1 | 9/2011 |
| EP | 2380509 A2 | 10/2011 |
| EP | 1983906 B1 | 11/2011 |
| EP | 2389878 A1 | 11/2011 |
| EP | 2010066 B1 | 12/2011 |
| EP | 2392268 A1 | 12/2011 |
| EP | 2409654 A2 | 1/2012 |
| EP | 1684641 B1 | 2/2012 |
| EP | 2412318 A2 | 2/2012 |
| EP | 2417916 A2 | 2/2012 |
| EP | 1399072 B1 | 3/2012 |
| EP | 2446838 A2 | 5/2012 |
| EP | 2455007 A2 | 5/2012 |
| EP | 2455012 A2 | 5/2012 |
| EP | 2462880 A2 | 6/2012 |

(56) References Cited

FOREIGN PATENT DOCUMENTS

| | | |
|---|---|---|
| EP | 2019633 B1 | 8/2012 |
| EP | 2497431 A1 | 9/2012 |
| EP | 2520228 A2 | 11/2012 |
| FR | 2598905 A1 | 11/1987 |
| FR | 2815842 A1 | 5/2002 |
| GB | 1530282 A | 10/1978 |
| GB | 2150440 A | 7/1985 |
| GB | 2177748 A | 1/1987 |
| GB | 2190297 A | 11/1987 |
| GB | 2226958 A | 7/1990 |
| GB | 2443736 A | 5/2005 |
| RU | 2093201 C1 | 10/1997 |
| RU | 2110221 C1 | 5/1998 |
| RU | 2196530 C1 | 1/2003 |
| RU | 2245113 C2 | 1/2005 |
| RU | 2261057 C1 | 9/2005 |
| RU | 2299023 C2 | 5/2007 |
| RU | 200814150 A | 5/2010 |
| WO | 9309717 A1 | 5/1993 |
| WO | 9415535 A1 | 7/1994 |
| WO | 9602279 A2 | 2/1996 |
| WO | 9619146 A1 | 6/1996 |
| WO | 9846301 A1 | 10/1998 |
| WO | 9913780 A1 | 3/1999 |
| WO | 9918858 A1 | 4/1999 |
| WO | 9920183 A1 | 4/1999 |
| WO | 0032113 A1 | 6/2000 |
| WO | 0054662 A1 | 9/2000 |
| WO | 0110306 A1 | 2/2001 |
| WO | 0128432 A1 | 4/2001 |
| WO | 0143649 A1 | 6/2001 |
| WO | 0224080 A2 | 3/2002 |
| WO | 02082975 A2 | 10/2002 |
| WO | 02087425 A2 | 11/2002 |
| WO | 03011150 A1 | 2/2003 |
| WO | 03022159 A1 | 3/2003 |
| WO | 03037162 A2 | 5/2003 |
| WO | 03041596 A1 | 5/2003 |
| WO | 03053256 A1 | 7/2003 |
| WO | 03082076 A2 | 10/2003 |
| WO | 03082129 A2 | 10/2003 |
| WO | 03086206 A1 | 10/2003 |
| WO | 03/090633 A2 | 11/2003 |
| WO | 03096881 A2 | 11/2003 |
| WO | 2004004542 A2 | 1/2004 |
| WO | 2004023976 A2 | 3/2004 |
| WO | 2004026148 A1 | 4/2004 |
| WO | 2004026201 A1 | 4/2004 |
| WO | 2004032761 A1 | 4/2004 |
| WO | 2004045370 A2 | 6/2004 |
| WO | 2004058079 A2 | 7/2004 |
| WO | 2004066846 A1 | 8/2004 |
| WO | 2004110285 A1 | 12/2004 |
| WO | 2005027721 A2 | 3/2005 |
| WO | 2005046453 A2 | 5/2005 |
| WO | 2005060838 A2 | 7/2005 |
| WO | 2005063133 A1 | 7/2005 |
| WO | 2005072105 A2 | 8/2005 |
| WO | 2005060838 A3 | 9/2005 |
| WO | 2005086824 A2 | 9/2005 |
| WO | 2005096960 A1 | 10/2005 |
| WO | 2005120326 A2 | 12/2005 |
| WO | 2006009545 A1 | 1/2006 |
| WO | 2006042110 A2 | 4/2006 |
| WO | 2006085389 A1 | 8/2006 |
| WO | 2006102578 A1 | 9/2006 |
| WO | 2007009099 A2 | 1/2007 |
| WO | 2007016288 A2 | 2/2007 |
| WO | 2007019268 A2 | 2/2007 |
| WO | 2007019321 A2 | 2/2007 |
| WO | 2007025014 A2 | 3/2007 |
| WO | 2007090291 A1 | 8/2007 |
| WO | 2007106342 A2 | 9/2007 |
| WO | 2008020975 A2 | 2/2008 |
| WO | 2008024671 A2 | 2/2008 |
| WO | 2008024672 A2 | 2/2008 |
| WO | 2008033558 A2 | 3/2008 |
| WO | 2008070763 A1 | 6/2008 |
| WO | 2008137833 A2 | 11/2008 |
| WO | 2009005527 A1 | 1/2009 |
| WO | 2005046453 A3 | 4/2009 |
| WO | 2009094078 A2 | 7/2009 |
| WO | 2009108464 A1 | 9/2009 |
| WO | 2009129369 A1 | 10/2009 |
| WO | 2009135022 A1 | 11/2009 |
| WO | 2009136397 A2 | 11/2009 |
| WO | 2010006028 A1 | 1/2010 |
| WO | 2010011661 A1 | 1/2010 |
| WO | 2010055232 A1 | 5/2010 |
| WO | 2010080386 A2 | 7/2010 |
| WO | 2010091913 A1 | 8/2010 |
| WO | 2011019848 A1 | 2/2011 |
| WO | 2011025877 A1 | 3/2011 |
| WO | 2011028196 A2 | 3/2011 |
| WO | 2011050658 A1 | 5/2011 |
| WO | 2011057282 A2 | 5/2011 |
| WO | 2011060386 A2 | 5/2011 |
| WO | 2011066533 A1 | 6/2011 |
| WO | 2011078959 A1 | 6/2011 |
| WO | 2011081791 A1 | 7/2011 |
| WO | 2011083027 A1 | 7/2011 |
| WO | 2011091185 A1 | 7/2011 |
| WO | 2011112577 A1 | 9/2011 |
| WO | 2012021082 A2 | 2/2012 |
| WO | 2012021207 A1 | 2/2012 |
| WO | 2012048387 A1 | 4/2012 |
| WO | 2012064643 A1 | 5/2012 |
| WO | 2012125621 A1 | 9/2012 |
| WO | 2012126477 A1 | 9/2012 |
| WO | 2012129317 A2 | 9/2012 |

OTHER PUBLICATIONS

International search report and written opinion dated Sep. 17, 2008 for PCT/US2007/068147.
International Search Report and Written Opinion dated Oct. 12, 2010 for PCT/US2010/045216.
Office action dated Jan. 31, 2013 for U.S. Appl. No. 12/849,534.
Office action dated Feb. 24, 2012 for U.S. Appl. No. 13/180,373.
Office action dated Dec. 7, 2010 for U.S. Appl. No. 11/744,135.
Response to final office action dated Aug. 1, 2012 for U.S. Appl. No. 11/155,305.
Response to office action dated Apr. 28, 2009 for U.S. Appl. No. 11/155,305.
Revised Brief on Appeal dated Sep. 7, 2010 for U.S. Appl. No. 11/003,696.
Salzberg et al., "Surgical left atrial appendage occlusion: evaluation of a novel device with magnetic resonance imaging" Eur J Cardiothorac Surg (2008) 34:766-770. Retrieved from the Internet: < http://ejcts.ctsnetjournals.org/cgUreprint/34/4/766>.
Supplemental EP Search Report dated Feb. 3, 2014 for EP Patent Application No. 07761828.8, 5 pages.
Burke, Redmond P., et al., "Improved Surgical Approach to Left Atrial Appendage Aneurysm", Journal of Cardiac Surgery, 1992, vol. 7, No. 2, pp. 104-107.
Johnson, W. Dudley, et al., "The left atrial appendage: our most lethal human attachment! Surgical implications", European Journal of Cardio-thoracic Surgery, 2000, vol. 17, pp. 718-722.
Cox, James L., "The surgical treatment of atrial fibrillation", J. Thorac. Cardiovasc. Surg., 1991, vol. 101, pp. 584-592.
Madden, John L., MD, "Resection of the Left Auricular Appendix", J.A.M.A., Jul. 2, 1949, vol. 140, No. 9, pp. 769-772.
Bonow, Robert O., et al., "Guidelines for the Management of Patients With Valvular Heart Disease: Executive Summary: A Report of the American College of Cardiology/American Heart Association Task Force on Practice Guidelines (Committee on Management of Patients With Valvular Heart Disease)", Circulation J.A.M.A., 1998, vol. 98, pp. 1949-1984.
Halperin, Jonathan L., MD, FACC, et al., "Obliteration of the Left Atrial Appendage for Prevention of Thromboembolism", Journal of the American College of Cardiology, 2003, vol. 42, No. 7, pp. 1259-1261.

(56) References Cited

OTHER PUBLICATIONS

Bohm, Jurgen, et al., "Surgical removal of atrial septal defect occlusion system-devices", European Journal of Cardio-thoracic Surgery, 1997, vol. 12, pp. 869-872.

Stollberger, Claudia, MD, et al., "Elimination of the Left Atrial Appendage to Prevent Stroke or Embolism?: Anatomic, Physiologic, and Pathophysiologic Considerations", Chest, Dec. 2003, vol. 124, No. 6, pp. 2356-2362.

Al-Saady, N. M., et al., "Left atrial appendage: structure, function, and role in thromboembolism", Heart, 1999, vol. 82, pp. 547-554.

Sievert, Horst, et al., "Percutaneous Left Atrial Appendage Transcatheter Occlusion to Prevent Stroke in High-Risk Patients With Atrial Fibrillation: Early Clinical Experience", Circulation J.A.M.A., Apr. 23, 2002, pp. 1887-1889.

Millennium Research Group's Physician Forum, "Stroke Prevention in Atrial Fibrillation: Is there a Future for Left Atrial Appendage Occlusion?: A Survey of Current Practitioners and Potential Adopters in the US and Europe", Dec. 2010, 66 pages.

Coffin, Laurence H., MD, et al., "Use of the Surgical Stapler to Obliterate the Left Atrial Appendage", Surgery, Gynecology & Obstetrics, Jun. 1985, vol. 160, No. 6, pp. 565-566.

Landymore, R., MD, et al., "Staple Closure of the Left Atrial Appendage", The Canadian Journal of Surgery, Mar. 1984, vol. 27, No. 2, pp. 144-145.

Disesa, Verdi J. MD, et al., "Ligation of the Left Atrial Appendage Using an Automated Surgical Stapler", The Annals of Thoracic Surgery, 1988, vol. 46, pp. 652-653.

\* cited by examiner

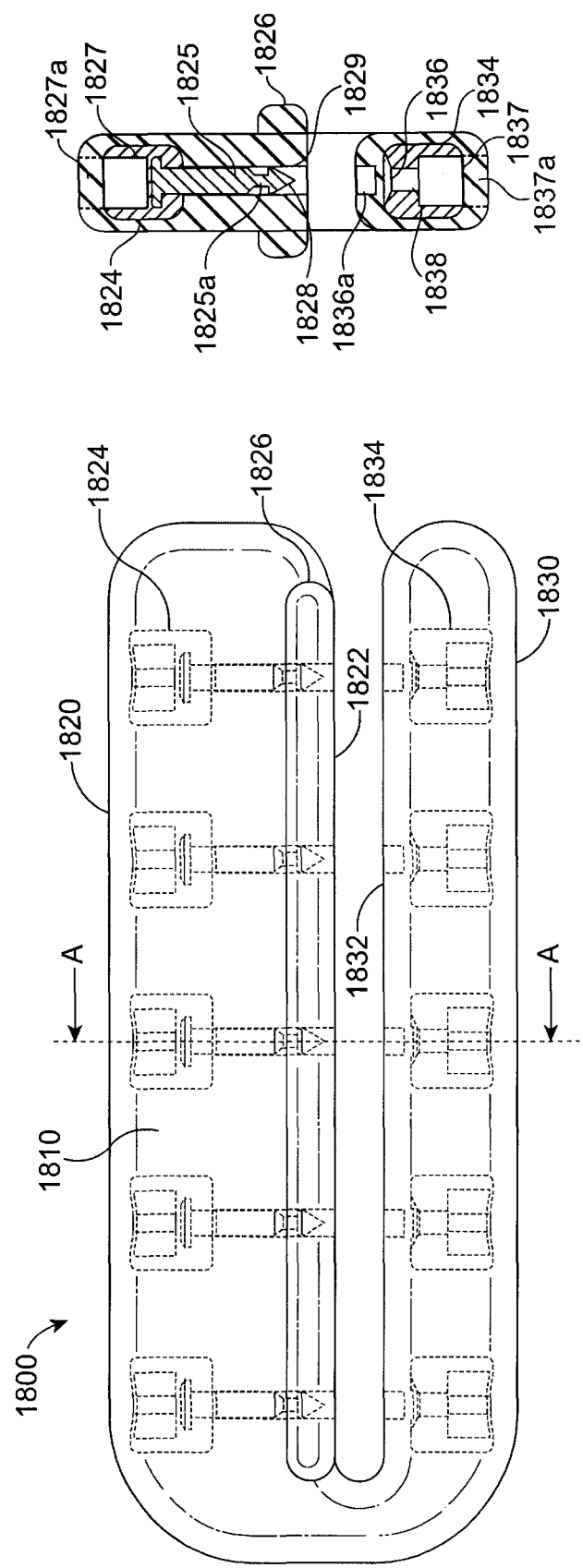

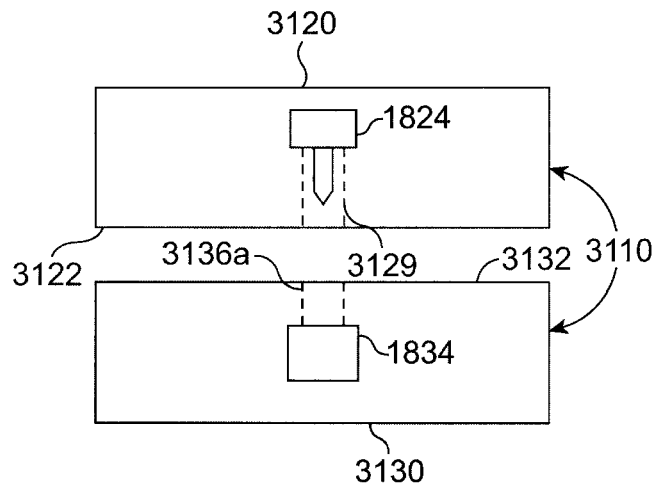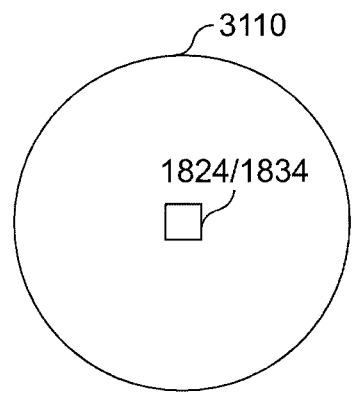
FIG. 31A  FIG. 31B
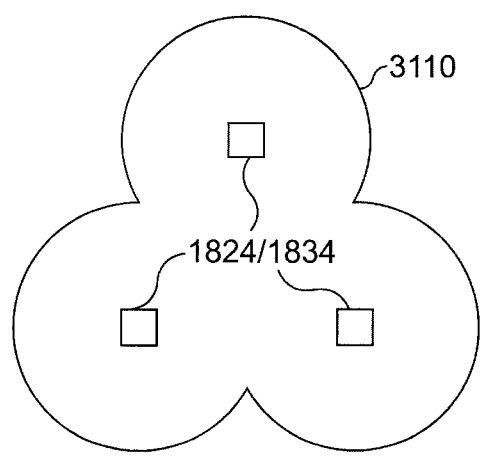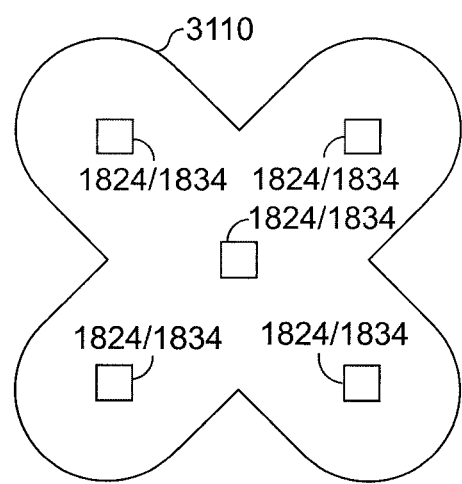
FIG. 31C  FIG. 31D

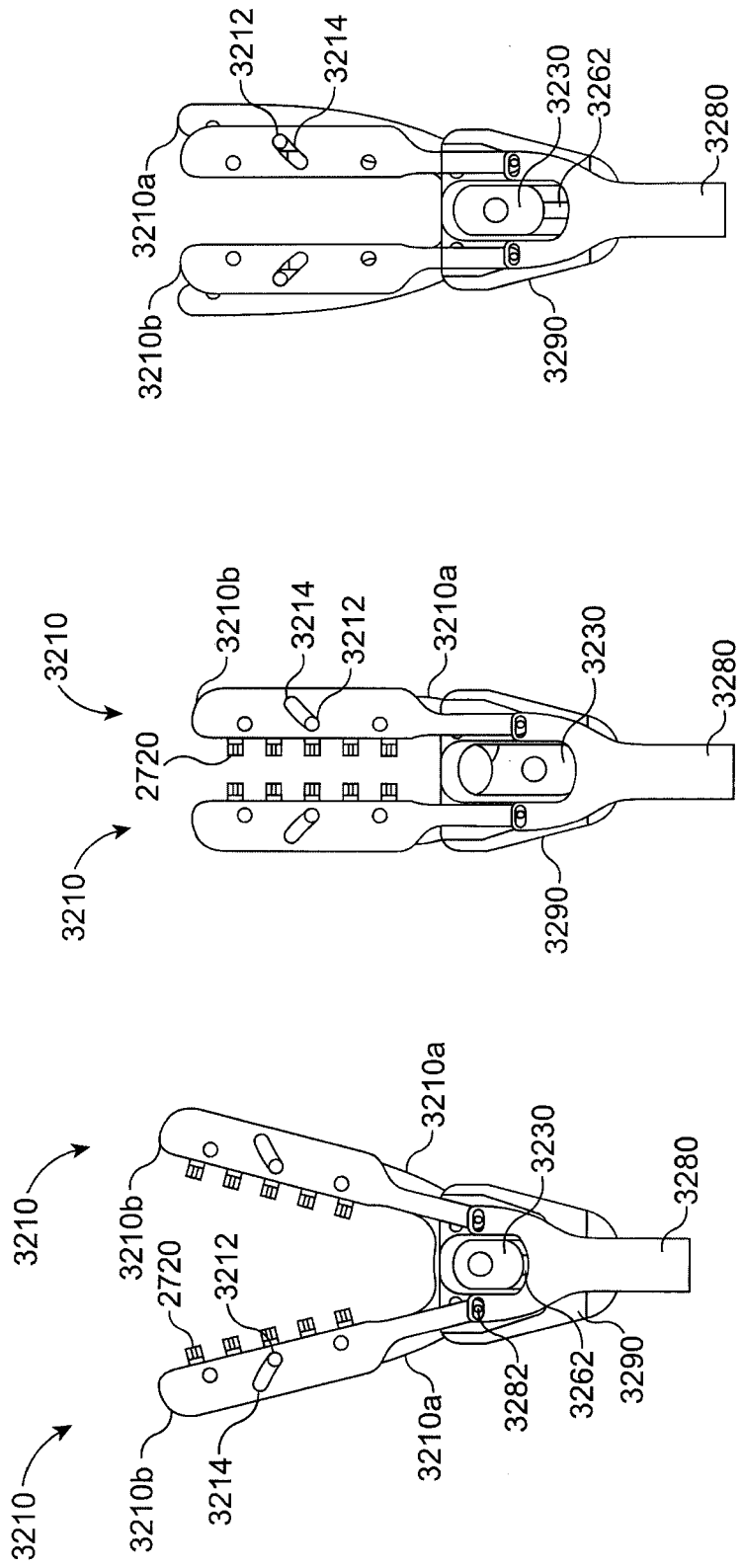

SYSTEMS AND METHODS OF TISSUE CLOSURE

CROSS REFERENCE TO RELATED APPLICATIONS

This application is a continuation of U.S. patent application Ser. No. 13/180,373 (U.S. Pat. No. 8,561,872), filed Jul. 11, 2011, which is a divisional of U.S. application Ser. No. 11/744,135 (U.S. Pat. No. 7,992,757), filed May 3, 2007, which claims the benefit of priority from U.S. Provisional Application No. 60/797,461, filed May 3, 2006, the contents of which are incorporated herein by reference.

BACKGROUND OF THE INVENTION

1. Field of the Invention

The present invention relates generally to medical devices, systems, and methods. More particularly, the present invention relates the closure and removal of a left atrial appendage or other tissue structure using a compliant compression body for isolating the structure near its base.

Atrial fibrillation is a relatively common condition characterized by a very rapid heart beat of the left and right atrium. While atrial fibrillation is not normally fatal itself, it has been associated with an increased risk of stroke. It is believed that the rapid heart beat causes blood to pool in the left atrial appendage which causes emboli that are released into the left atrium from where they can enter the cerebral vasculature, thus causing a stroke. In addition to stroke, the emboli can enter coronary circulation, potentially causing myocardial infarction, or can enter peripheral circulation, potentially causing peripheral vascular disease.

The risk of stroke in patients suffering from atrial fibrillation can be reduced in a variety of ways. For example, blood thinning drugs can be used to reduce the risk of clot formation. The use of blood thinners, however, is contraindicated in patients at risk of bleeding disorders.

More aggressive treatment protocols have been proposed which involve closing the left atrial appendage. Closure and excision may be performed in open surgical procedures, typically requiring the patient to be placed on by-pass and the chest to be opened through the sternum. Alternatively, thoracoscopic and other less invasive procedures have been proposed. U.S. Pat. No. 5,306,234 teaches the performance of beating heart procedures using otherwise conventional surgical techniques. The use of conventional techniques through small chest penetrations while the heart is beating can be difficult to perform. U.S. Pat. No. 5,865,791 describes an intravascular approach where tools are introduced through the vasculature and passed into the left atrium. The tools are used to ablate or fuse the left atrial appendage from the inside using energy, adhesives, or the like. The '791 patent also describes a thoracoscopic procedure where a tether is placed over the neck of the atrial appendage and tied off to achieve isolation. The '791 patent still further suggests other closure elements including sutures, staples, shape-memory wires, biocompatible adhesives, and the like. U.S. Pat. No. 6,488,689 describes a transpericardial procedure where the distal tip of the left atrial appendage is grasped and pulled backwardly through a capture loop which encircles the base of the left atrial appendage.

For these reasons, it would be desirable to provide improved apparatus, systems, and methods for less invasively closing the left atrial appendage and other body structures. Such apparatus, systems, and methods should be capable of being performed on beating hearts, should avoid the need to form a transeptal penetration to access the left atrium, and very importantly should result in tissue closure at the base of the left atrial appendage. In addition to the above, it would be still further desirable if the methods and protocols were relatively easy to perform and the closure element and other aspects of the device produce a secure closure. At least some of these objectives will be met by the inventions described herein below.

2. Description of the Background Art

Less invasive and other procedures for closing the left atrial appendage are described in U.S. Pat. Nos. 6,488,689; 5,865,791; and 5,306,234; and Published Application Nos. 2005/0154404 and 2004/0030335. Other tissue ligation tools and techniques are described in U.S. Pat. Nos. 6,790,172; 6,436,108; 6,051,003; 5,624,453; 5,507,797; and 4,257,419.

BRIEF SUMMARY OF THE INVENTION

The present invention provides alternative and improved apparatus, systems, and methods for closing a tissue structure. Embodiments of the present invention provide a tissue closure device that includes a compression body with two opposing compliant surfaces for engaging either side of the tissue structure. The compliant surfaces preferably have a softness matching that of the tissue structure. The closure device preferably have a flexibility and dynamic performance similar to that of the tissue structure. Fasteners are disposed in the compression body adjacent the opposing compliant surfaces and at least one tissue-piercing fastener is configured to emerge from a first compliant surface, pass through the intervening tissue at a puncture site to the second compliant surface, and securely engage a second fastener compress the tissue between the two surfaces. An open well may be disposed in either or both of the compliant surfaces around the puncture site where the tissue-piercing fastener passes through the intervening tissue to create a gasket seal around the puncture site. A stabilizing lip may be provided on one of the compliant surfaces such that one surface is larger than the other surface. Vacuum ports may also be provided in the compliant surfaces to engage the surface of the tissue structure. Fasteners of the closure device may include open lumens or recesses for interacting with a device applicator used to install the closure device.

Embodiments of the present invention provide a system for tissue closure that includes a tissue closure device and a device applicator used to install the device. The applicator may include two opposing jaws or prongs used to hold open two opposing legs of the closure device, and to bring the legs together to engage the fasteners and install the device. An alignment comb may be used having studs that engage each one of the fasteners in the closure device. The alignment comb may be received within inner jaws of the applicator which may be moved independently of the outer jaws to release the closure device after installation is complete. Vacuum lumens may be provided in each of the jaws that communicate with the vacuum ports of the closure device to provide suction to the ports. The jaws or probes may move in a parallel manner with respect to each other or may move about a pivot point. The applicator may include a handle mechanism for actuating the movement of the jaws.

Embodiments of the present invention provide a method for implanting a tissue closure device about the base of a left atrial appendage (LAA). The procedure may be performed thoracoscopically using a thoracoscope introduced in the region above the LAA after the left lung has been deflated. The procedure can be performed under direct vision through the same incision through which the applicator is introduced or through a separate incision formed over the region of the LAA. The tissue closure applicator is introduced intercostally, the probes are then spread apart, spreading the legs of the closure device. After the legs are located on opposite sides of the LAA, the legs will be pressed downwardly on to the cardiac tissue surrounding the base of the appendage. The vacuum may then be optionally applied through the legs of the closure device, adhering the legs to the cardiac surface. After the proper position is visually confirmed, the applicator will be mechanically closed over the base of the LAA. The applicator may then be triggered to deliver the male fasteners into the female fasteners. The tissue closure applicator may then be disengaged from the installed closure device.

Further aspects and advantages of the present invention will be apparent in view of the following detailed description of the preferred embodiments.

BRIEF DESCRIPTION OF THE DRAWINGS

FIG. 19 is an elevation view of the tissue closure device of FIG. 18.

FIG. 20 is cross-sectional view of the tissue closure device along line A-A of FIG. 19.

FIG. 31A is a cross-sectional view of another embodiment of the tissue closure device constructed in accordance with the principles of the present invention.

FIG. 31B is a top plan view of the tissue closure device of FIG. 31A.

FIG. 31C is a top plan view of another embodiment of the tissue closure device constructed in accordance with the principles of the present invention.

FIG. 31D is a top plan view of another embodiment of the tissue closure device constructed in accordance with the principles of the present invention.

FIG. 33A is an elevation view showing the jaws of the applicator open to receive the closure device.

FIG. 33B is an elevation view showing the jaws of the applicator closed to install the closure device.

FIG. 33C is an elevation view showing the inner jaws moving apart independently of the outer jaws to disengage the comb studs from the installed closure device.

DETAILED DESCRIPTION OF THE INVENTION

Figure 1:
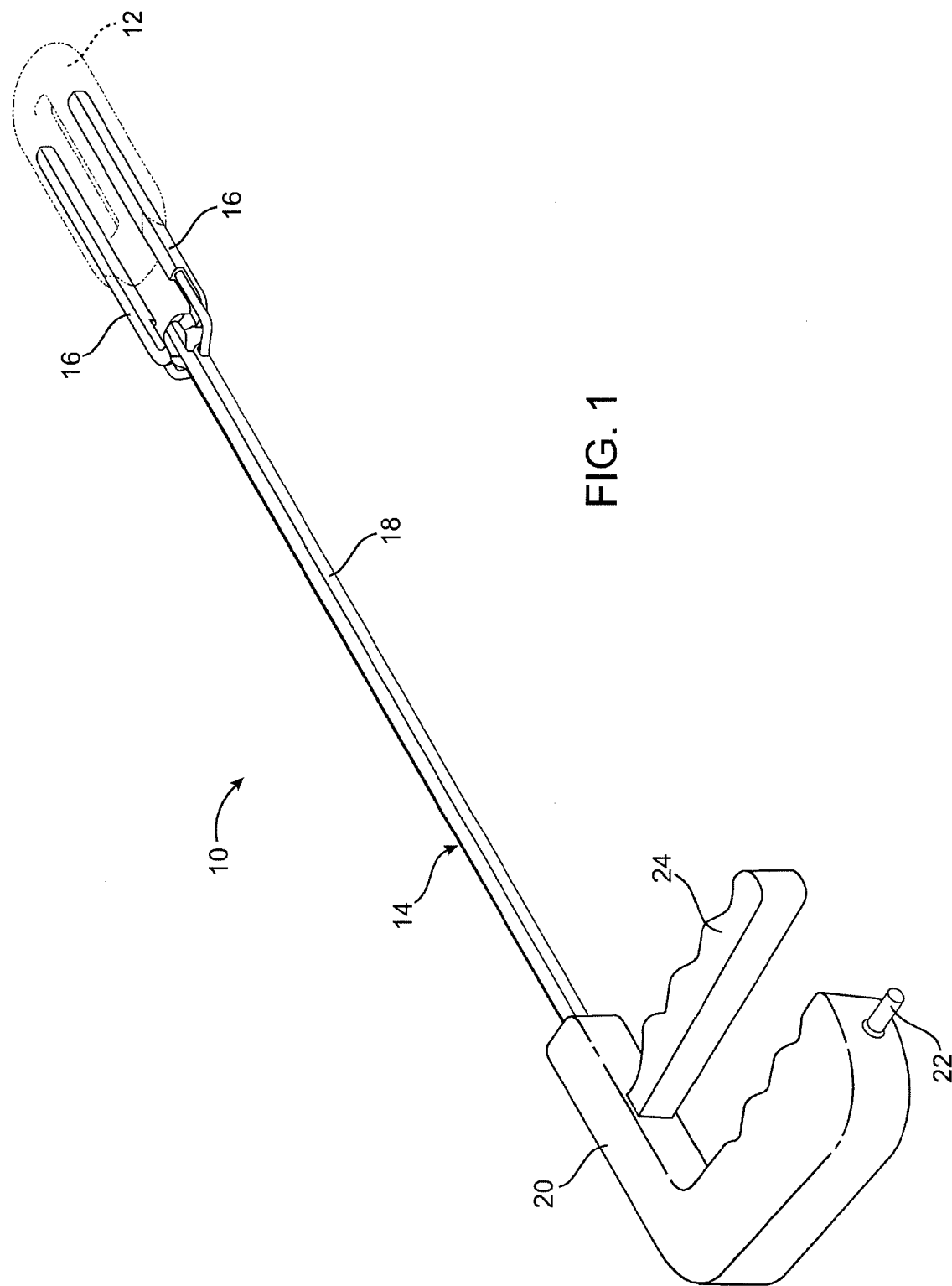
FIG. 1 is an isometric view of one embodiment of a tissue closure applicator constructed in accordance with the principles of the present invention. An exemplary tissue closure device is shown in broken line mounted on the distal end of the tissue closure applicator.

The present invention provides alternative and improved apparatus, systems, and methods for closing a tissue structure of a patient, for example, a left atrial appendage in a patient at risk of stroke or other adverse events resulting from emboli released into circulation from the left atrial appendage. Patients benefiting from the procedures of the present invention will often be those suffering from atrial fibrillation which can cause clot and thrombus formation in the left atrial appendage, thus increasing the chance of emboli release.

The present invention provides a tissue closure device which is an implant introduced over the base of the tissue structure and left in place to close the tissue structure at the base. The portion of the tissue structure which is over the base may then be excised or otherwise removed, although this may be left be left to the physician's preference. The tissue closure device comprises a compression body having at least two opposed, compliant tissue-engaging surfaces which will be placed over opposite sides of the tissue structure. The tissue-engaging surfaces will be held together by a plurality of axially spaced-apart tissue-penetrating fasteners which extend from one of the surfaces, through the intermediate tissue, and into the other surface to both hold the compression body in place and to apply a desired level of compression force, which is determined by both the softness of the compression body and the distance between the surfaces when they are fully attached. A well may be provided in the compression body around the tissue-penetrating barb of the fastener such that a gasket seal is formed by the compression body around the puncture site in the tissue. A stabilizing lip may be provided in one leg of the compression body to prevent a rolling motion of one leg with respect to another leg of the compression body.

The compression force applied by the closure device can be varied, for example, by controlling the distance between the surfaces and/or by providing one or more barbs, detents, or other spaced-apart attachment points which permit the tissue-engaging surfaces to be "ratcheted" together. In this way, the tissue-engaging surfaces can be closed with a predetermined closure force, as described below, with the resulting spacing between the tissue-engaging surfaces varying to accommodate tissue structures having different widths. That is, tissue-engaging surfaces of the closure device will be closed with the predetermined force until such point that the tissue is deformed with a counter force that holds the tissue-engaging surfaces apart. The fasteners will then lock in at the attachment point which most closely approximates this spacing between the tissue-engaging surfaces. Typically, there may be from 1 to 20 attachment points along the length of the fastener, typically from 2 to 8 attachment points, although in special cases, more than 20 attachment points will be affixed. Other, non-linear arrangements of fasteners can also be used. A particular advantage of the fastener structure is that the fasteners will preferably never extend beyond the exterior perimeter of the compression body after deployment. While the penetrating fasteners will be able to penetrate tissue, they will not be able to penetrate outside of the compression body to place adjacent tissue structures at risk.

A particular advantage of the compression body of the present invention is that it provides an "interrupted" attachment of the conformable surfaces on either side of the appendage or other tissue structure, which is similar to closure with "interrupted suture." Prior closure devices, such as loops, lassoes, staples, and the like, can provide a very tight and hemostatic seal, but the seal is often too tight and traumatic and will cause tissue necrosis at the closure region at the base of the structure. The use of the tissue fasteners which are spaced-apart and bridged only by a soft compliant tissue-engaging surface will provide an adequate hemostatic seal while at the same time significantly reducing the risk of tissue necrosis within the sealed region, applying the same closure effectively as "interrupted suture." The soft compliant tissue engaging surface functions to tack down the layers of tissue between the seal, as well as to provide the spacing required between male and female fasteners. The combination of the soft compliant tissue engaging surface and the properly spaced apart fasteners result in little or no necrosis and erosion in the compressed tissue and its surrounding tissue areas, even in the dynamic environment of a beating heart.

In some embodiments, however, tissue necrosis may actually be desirable distal to the closure device, and it is possible to control tissue necrosis by varying the durometer of the compliant material used in the body of the device or by baffling the body material itself to allow hollow or open areas to add to its softness. Also, the amount of tissue necrosis may be controlled by increasing or decreasing the spacing between the fasteners on each side of the device, and by increasing or decreasing the installed distance between the male and female fasteners.

The compliant surfaces of the compression body will typically have a durometer in the range from 3 shore A to 15 shore A, more preferably from 3 shore A to 5 shore A. Suitable materials for the compliant tissue engaging surface portions of the compression body include silicone, polyurethane, and other soft, biologically compatible polymers. The use of such soft materials provides a three-dimensional compliance so that the tissue-engaging surfaces will conform to the three-dimensional topography of the tissue after it has been compressed as described above, and averts the potential to cause significant damage to the patient's tissue due to compliance mismatch. It is preferred that the compliance of the compression body, or at least the tissue engaging surfaces of the compression body, matches the compliance of the tissue to which the closure device is applied. Moreover, the installed closure device will preferably behave dynamically in the same manner as the patient's tissue surrounding the device. For example, the density and flexibility of the compression body material, the amount of material used for the compression body as compared to the number of rigid fasteners, the geometric configuration of the fasteners within the compression body, the installed distance between male and female fasteners (affecting the amount of compression placed on the intervening tissue), and the existence of any framework material interconnecting the fasteners in the compression body may all contribute to the dynamic performance of the device.

In the exemplary embodiments described hereinafter, the compression bodies may be composed entirely of the soft polymeric body material and the fastener components which are described below may be composed entirely of rigid materials. It will be appreciated, however, that the compression body could also have rigid frame, scaffold, or other components forming a portion of the body which is left in place as the implant. It is necessary only that the tissue-engaging surface of the compression body be formed from a compliant material which allows local conformance of the compression body to the tissue surface being engaged.

In some instances, it may be desirable to form all or a portion of the compression body from a biodegradable material. Certain biodegradable polymers, such as polylactic acids (PLA's), polyethyl glycol (PEG's), and polyglycolic acids (PGLA's) can be formulated to have both suitable durometers and to also to degrade in the thoracic or other body environment into which they are being implanted. Usually, it will be desirable to have the implant remain in a structurally competent form for a period of at least several weeks before significant degradation would occur. After that time, healing of the punctured tissue (e.g., the left atrial wall) will occur and the presence of the implant may no longer be necessary. When employing such a biodegradable compression body, it will also be desirable to have the tissue-penetrating fasteners formed from a biodegradable material, such as a suitable biodegradable polymer or possibly a biodegradable metal, such as an iron or steel fastener which will oxidize over a pre-selected time period.

The compliant and flexible compression body will usually comprise a pair of parallel, opposed legs having the tissue-engaging surface (usually planar) on a side of each leg. Parallel opposed legs may be joined at both ends, to form a continuous ring structure, at only one end, or at neither end, where they would be joined only after deployment of the tissue-penetrating fasteners after the member has been placed around the appendage or other tissue structure. In other instances, however, the opposed tissue-engaging surfaces could have non-parallel and/or non-planar surfaces. For example, the tissue-engaging surfaces could be curved, usually being concave so that there is an open space surrounded by the surfaces when the legs are brought together. Alternatively, the surfaces could be curved and convex so that the legs of the closure device will apply a greater force in the center than at the ends. In one alternative embodiment, the surface could employ an "ice cream scoop" 3D configuration in which the tissue engaging surfaces grab a spherical volume of tissue. Still further alternatively, the surfaces could be irregular or have any one of a variety of other particular geometries.

In another aspect of the present invention, the compression body further comprises a vacuum plenum, preferably within each leg of the compression body. The vacuum plenum will typically open up into a plurality of ports which will be engaged against tissue prior to deployment of the tissue-penetrating fasteners. The applied vacuum will help hold the closure in place and conform tissue in a desired manner relative to the compliant tissue body prior to final attachment of the compression body. Usually, the vacuum ports will be formed along a lower set face of the parallel legs, where the lower face is oriented at an angle relative to the vacuum ports. Typically, the lower face may be oriented perpendicularly relative to the direction of actuation of the tissue-penetrating fasteners. In other instances, however, the vacuum ports could be aligned in parallel with the direction of actuation of the fasteners, or could be aligned at virtually any other relative angle. In this way, the lower face of the compression body may be engaged against the base of the left atrial appendage or other tissue structure and held in place by the vacuum. Once the proper positioning of the compression body is confirmed, the vacuum will continue to hold the compression body in place while the tissue fasteners are deployed through tissue and permanently affix the legs of the compression body together.

The tissue-penetrating fasteners typically comprise male and female connectors aligned along the opposed tissue-engaging surfaces. Alternatively, the fasteners may comprise barbed needles which are aligned upon at least one of the tissue-engaging surfaces. The tissue-penetrating fasteners will, after deployment, preferably be spaced-apart by a distance of at least about 1 mm, preferably at least about 1.3 mm, and more preferably in the range from about 1.3 mm to 5 mm, and most preferably in the range from about 1.3 mm to 2.6 mm. Usually, there will be only one line of tissue-penetrating fasteners deployed from the compression body. In other instances two or more parallel lines of fasteners might be employed. The line of fasteners can include 1 to 20 fasteners, more usually 2 to 8 fasteners. Also, the fasteners could be aligned along either or both faces of the tissue-engaging surfaces in a zig-zag or other non-linear manner, appreciating however that they must extend over an axial length on each face, typically being at least about 2 mm, preferably at least about 5 mm, more preferably at least about 10 mm, and most preferably in the range from about 10 mm to 40 mm. Materials for the tissue penetrating fasteners include but are not limited to a titanium grade 5 or a stainless steel 316 LVM fastener or nitinol or ULTEM (which may be injection molded).

In another aspect of the present invention, systems for closing a tissue structure include a closure device in combination with a closure device applicator. The closure device applicator detachably secures and opens the closure device in order to place the closure device over or around the tissue structure. The closure device also includes a plurality of fasteners as generally described above. The closure device applicator may be inserted into a port or lumen of the fasteners or may be used with an alignment comb that engages the fasteners of the closure device. The closure device applicator may include a vacuum path which connects to the vacuum plenum within the closure device or applying a vacuum the closure device and the tissue structure when the device is over the tissue structure.

The closure device applicator generally includes an jaw mechanism which includes two probes or jaws. Each probe is adapted to detachably engage one leg of the compliant compression body, using either an alignment comb received by the probe or by inserting the probe into a port or lumen which opens into the vacuum plenum of the compression body. Thus, probes of the jaw mechanism can serve to physically support and hold open the closure device during deployment and to close the closure device and securely install the device into the tissue. The probes may also provide a vacuum to the compression body when it is desired to adhere the compression body to tissue prior to deployment of the fasteners.

The fasteners of the closure device will typically "float" within the compression body, with the probes or jaws of the closure device applicator providing the force necessary to push the fasteners together. In some instances, however, the fasteners may be linked by frames, wires, tethers, chains, or other interconnections in order to help control or limit movement of the fasteners before, during, or after deployment by the applicator. For example, the links could control spacing between adjacent fasteners or control the horizontal and/or vertical alignment of the fasteners. In one method of manufacturing the closure device, the fasteners may be injection molded from a harder thermoplastic such as ULTEM to a set spacing and length, for example, 6 fasteners that are 0.26 mm apart. Subsequently, the soft compression body could be injection molded over two sets of the 6 injection molded ULTEM fasteners to form a C shaped closure device connected at one end and free at the opposite end.

In another aspect of the present invention, a method for closing a left atrial appendage or other tissue structure comprises positioning a compression body over the tissue structure with at least two compliant tissue-engaging surfaces engaging opposite sides of the structure. Preferably, the surfaces will be closed over the appendage or other tissue structure with a pressure sufficient to provide hemostasis and sealing but without causing tissue necrosis, typically being in the range from 0.25 psi to 20 psi, preferably in the range between 0.25 psi and 1.5 psi. The compression body may be initially held in place by applying a vacuum through the compression body to adhere the tissue-engaging surfaces to the tissue structure, preferably to tissue surrounding the base of the tissue structure. After proper positioning of the compression body is confirmed, the fasteners are deployed from at least one of the tissue-engaging surfaces, through the tissue, and into the other of the surfaces to close the tissue structure.

Positioning the compression body typically comprises advancing the compression member via an open procedure or intercostally, i.e., between ribs, preferably between the ribs 3 and 4. Usually, the compression member will be held on the applicator described above, with the applicator first spreading the tissue-engaging surfaces so that the compression body may be placed over or around the tissue structure and positioned at the base of the tissue structure. After the positioning is completed, the legs of the compression body will be closed over the tissue (at a spacing to accommodate the thickness of the tissue therebetween). Optionally, the vacuum may be applied while the compression body is manipulated in order to assure proper positioning of the compression body and spreading of the tissue between the opposed tissue-engaging surfaces so that the pressure applied to the tissue is generally uniform along the length to be fastened.

The compression bodies will typically be positioned and/or attached using fasteners while the physician views a tissue structure through an optical scope during at least a portion of the procedure. Alternatively, the physician could directly view the tissue structure through a percutaneous opening, typically the same percutaneous opening that can be used to introduce the device applicator. The tissue closure device is delivered via a clamping tool or device application that has a set of probes or jaws that come together in either a scissor action or in parallel motion. The jaws are activated by an external force applied by the operator, which can be as a squeezing action, trigger action, push-pull action, or the like, on a handle of the device applicator. The jaws may also incorporate mechanical advantages such as a cam or arc that effectuates a linear "all at once" force that snaps all of the fasteners together simultaneously or in sequence.

Optionally, the vacuum applicators and plenums may be used to deliver substances to the tissue structure through the compression body. For example, after the fasteners have been delivered, the vacuum can be turned off and a therapeutic or other agent delivered through the lumens and plenums so that it is released from the compression body in the region of the base of the tissue structure. Exemplary substances which could be delivered include antibiotics, antiseptics, anti-inflammatories, anti-bacterial, and the like.

After all steps of the present invention have been generally completed, as described above, it is left to the medical professional whether to excise the left atrial appendage or other tissue structure at a location above the compression body. Additional uses for the present invention include efficient intravascular or extra-vascular clipping of an aneurysm sac or extra flesh during a tummy tuck, a stomach stapling procedure, a lung reduction procedure, or a bowel resection procedure. A pronged formation or star shaped deployment of the compression bodies may be used to encourage efficient bunching of tissue. Another approach utilizes a single-fastener closure device, which consists of one fastener surrounded by a soft compression material in a pillow-like structure. The single-tissue compression body may be utilized in procedures where a single point closure device is needed, such as in a femoral closure procedure or in a fallopian tube or a bile duct closure procedure. This single-fastener closure device effectively clamps off flow or shuts the tubular structure with out causing traumatic necrosis. A detailed description of the embodiments of the present invention with respect to the figures is set forth below.

Referring now to FIG. 1, a tissue closure system 10 in accordance with an embodiment of the present invention includes a tissue closure device 12 (shown in broken line) and a tissue closure applicator 14. The tissue closure device 12 is removably held on a pair of probes 16 located at the distal end shaft of 18 which is connected to a handle 20 at its proximal end. As will be described in more detail with references to FIG. 9-13, the probes 16 will be spreadable, i.e., either in a parallel fashion or in a pivotal fashion, and will be able to apply a vacuum, or alternatively an infusion source, through the tissue closure device 12. To that end, a port 22 is provided on the handle 20 for connection to the vacuum or infusion source. Additionally, the handle 20 comprises a trigger 24 which may be manually actuated in order to spread the probes 16 to facilitate delivery over the target tissue structure, as will be described in more detail below.

Figure 2:
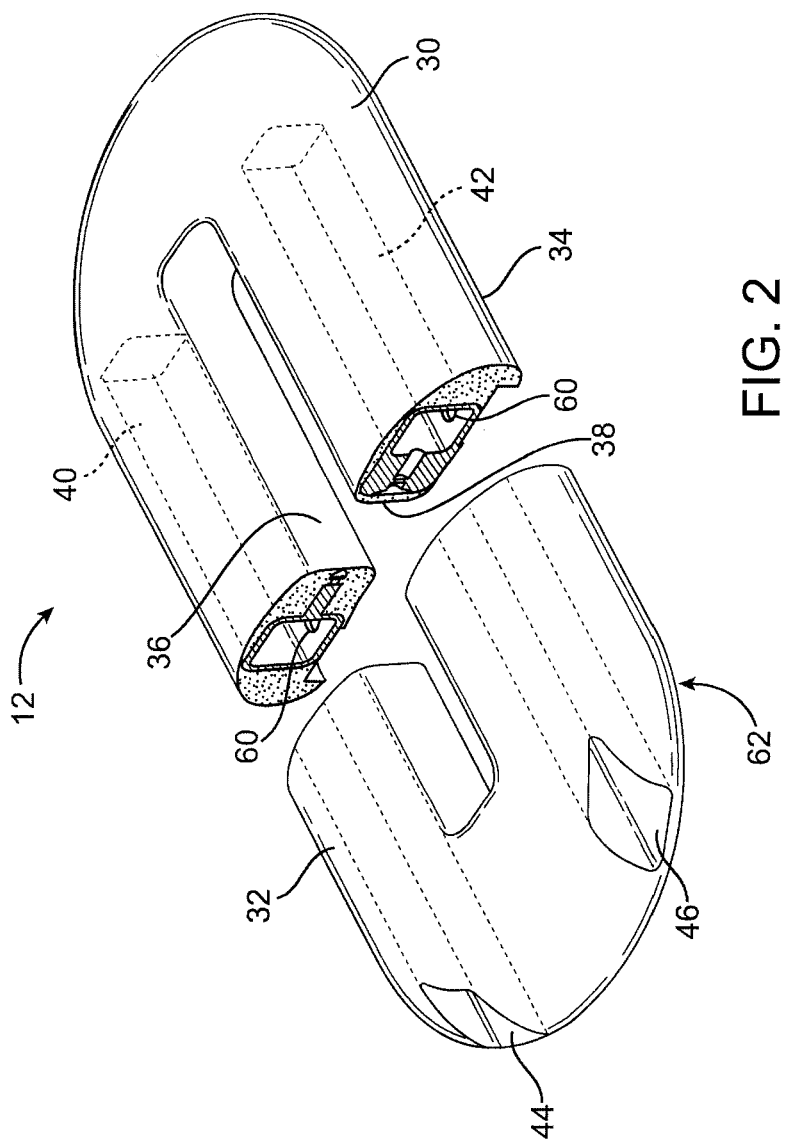
FIG. 2 is an isometric view of one embodiment of a tissue closure device constructed in accordance with the principles of the present invention, shown with a middle section broken away.
Figure 3:
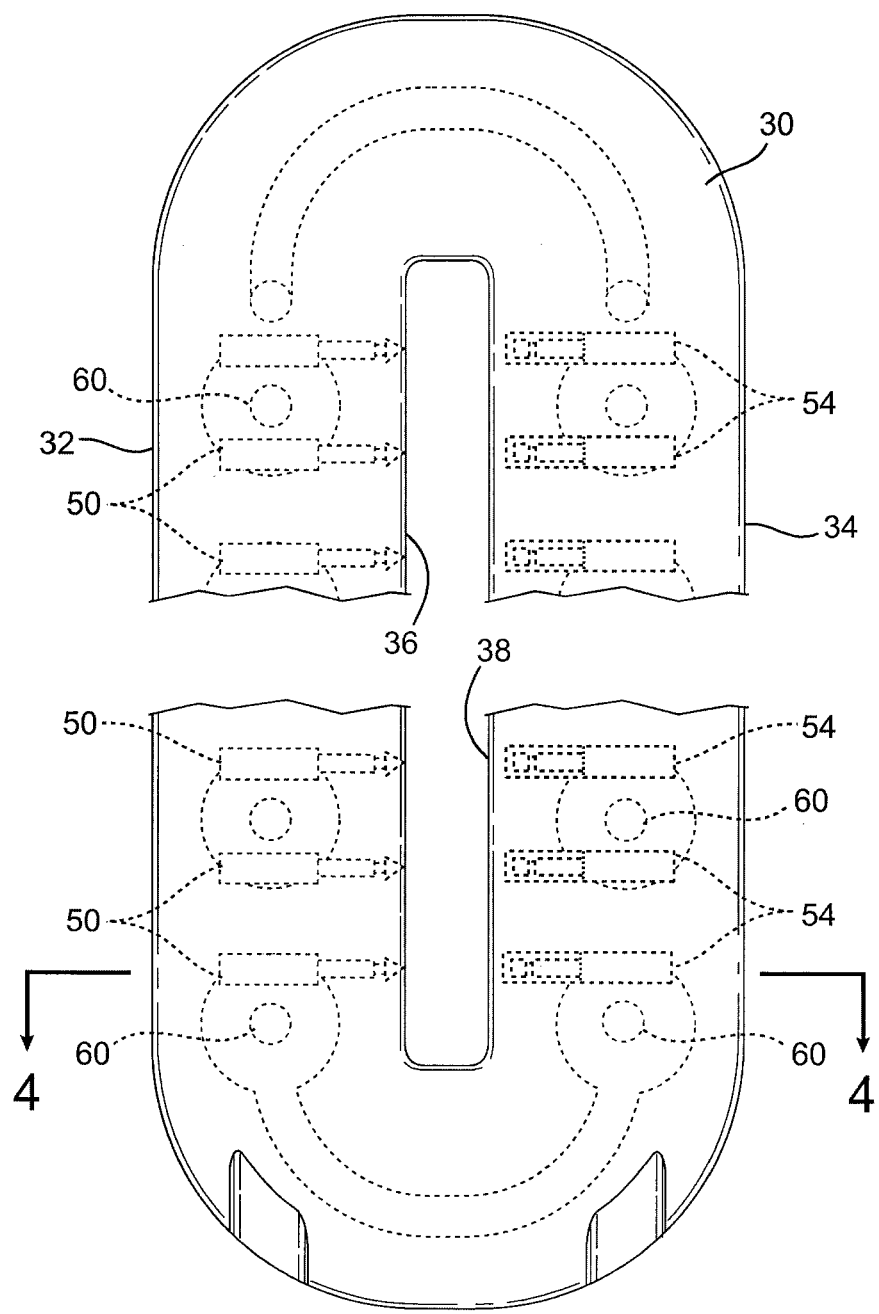
FIG. 3 is a top plan view of the tissue of closure device of FIG. 2.
Figure 4:
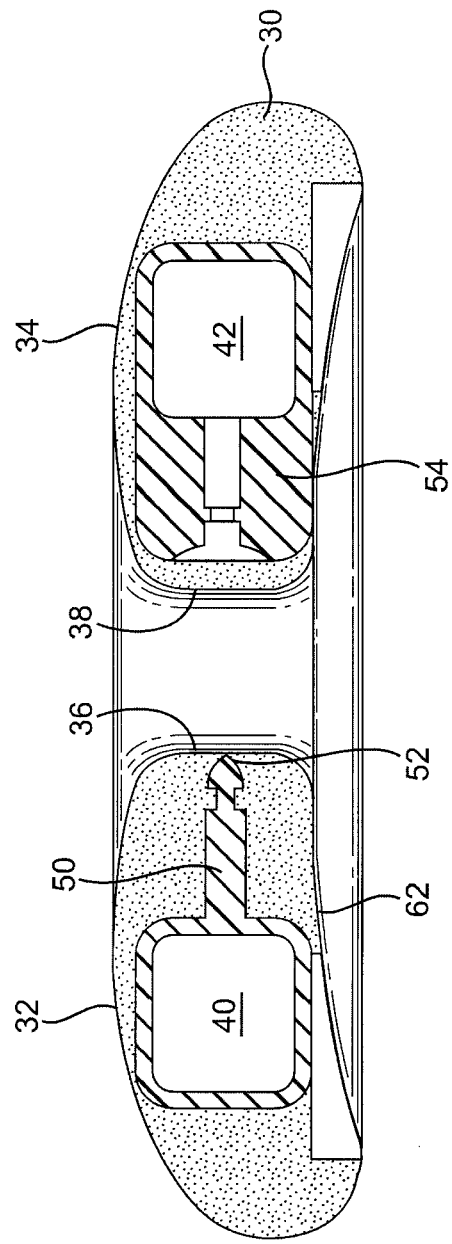
FIG. 4 is a cross-sectional view taken along line 4-4 of FIG. 3.
Figure 5A:
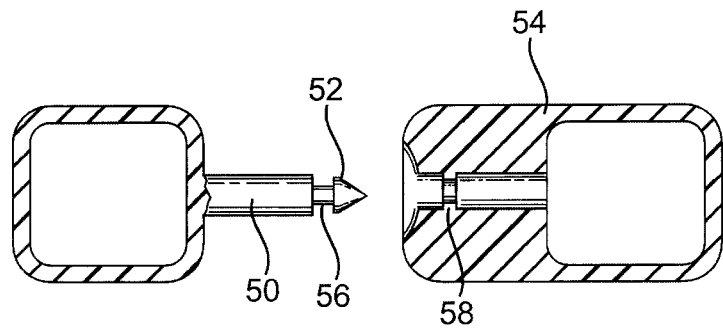
FIGS. 5A and 5B illustrate the fastener structures of the tissue closure device of FIGS. 2-4, shown in an unengaged configuration (FIG. 5A) and in an engaged configuration (FIG. 5B).
Figure 5B:
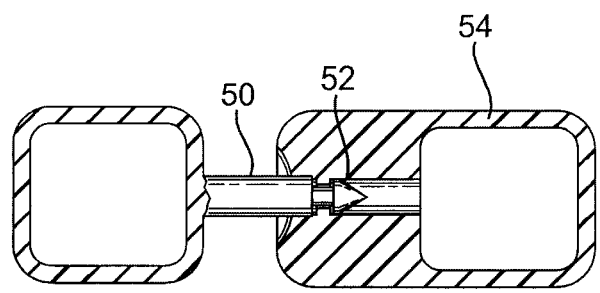

Referring now to FIGS. 2-4, which illustrates an embodiment of the tissue closure device in accordance with the present invention. In particular, tissue closure device 12 comprises a compression body 30, typically formed from silicone or other soft polymer. The compression body 30 comprises a pair of legs 32 and 34 having opposed tissue-engaging surfaces 36 and 38, respectively. Plenums 40 and 42 each terminate at an opening or port 44 and 46, respectively, which port receives one of the probes on the tissue closure applicator used in connection with the present embodiment. A plurality of fasteners will be provided in each of the legs 32 and 34, where the fasteners are adapted so that they will engage and couple each other when the closure device 12 is squeezed over tissue by the tissue closure applicator. As best seen in FIG. 4, a series of spaced-apart male fasteners 50 are aligned in leg 32 so that sharpened tips 52 may be advanced laterally into the opening between surfaces 36 and 38. Similarly, a series of axially spaced-apart female fasteners 54 are arranged in leg 34 to receive the male portions of fasteners 50 when the applicator probes are squeezed together. As best shown in FIGS. 5A and 5B, the sharpened tip 52 has an annual groove 56 which is received and locked over a shoulder 58 formed in the female fastener 54. In this way, spacing between the opposed tissue-engaging surfaces 36 and 38 can be carefully controlled at a distance selected to provide proper compression while reducing the risk of tissue necrosis.

Figure 5C:
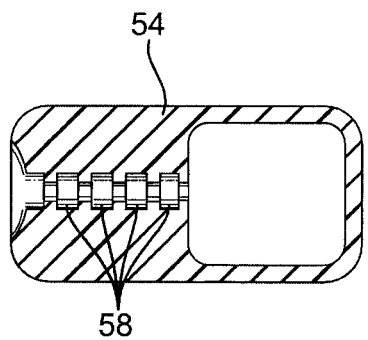
FIG. 5C shows a female fastener which is able to accommodate different tissue thicknesses.

As shown in FIG. 5C, the female fasteners 54 may have a plurality of shoulders 58 formed along their lengths in order to accommodate the groove 56 of the male fastener 50 at a variety of depths. Thus, the fasteners 50 and 54 can accommodate tissue having different thicknesses with essentially the same compression force.

As additionally seen in FIGS. 2-4, the tissue compression devices will have a plurality of vacuum ports 60 formed over the lower surface 62 thereof. These vacuum ports 60 communicate with the plenums 40 and 42 so that vacuum applied in the plenums will draw against tissue beneath the tissue closure device 12. In this way, the tissue closure device 12 can be initially adhered to tissue prior to actuation of the fasteners in the device. The physician can manually reposition the closure device using the tissue closure applicator, turning on and off the vacuum as necessary, until the tissue is contacted as close to the base of the left atrial appendage or other tissue structure as possible. Additionally, the tissue can be adjusted so that folds and surface discontinuities are minimized so that when the tissue closure 12 is closed and the fasteners deployed, the tissue between the tissue-engaging surfaces will be relatively smooth and the pressure applied will be relatively constant over the tissue surfaces. In this way, the risk of tissue necrosis is further diminished.

Figure 6:
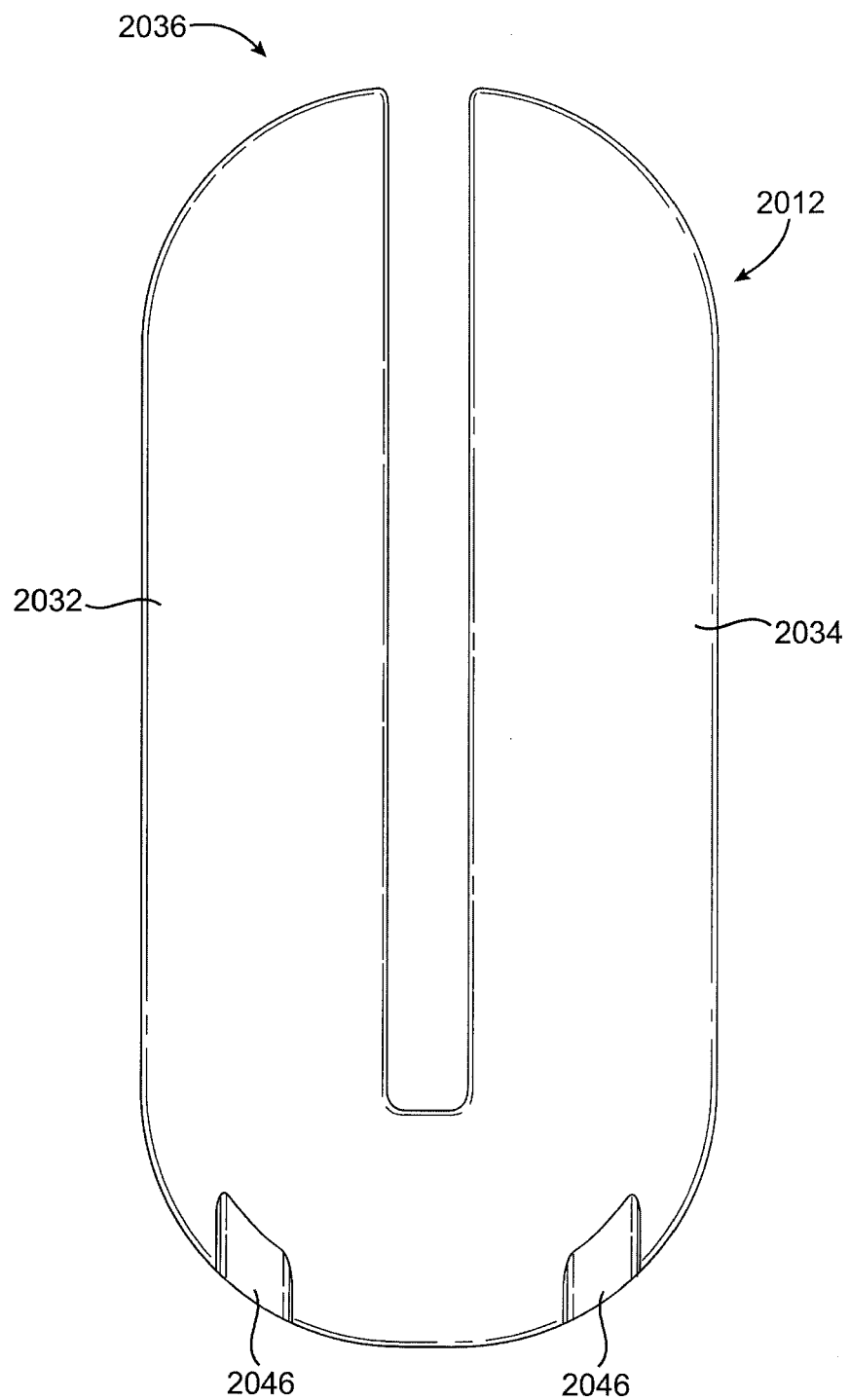
FIG. 6 is a top plan view of another embodiment of a tissue closure device constructed in accordance with the principles of the present invention.
Figure 7:
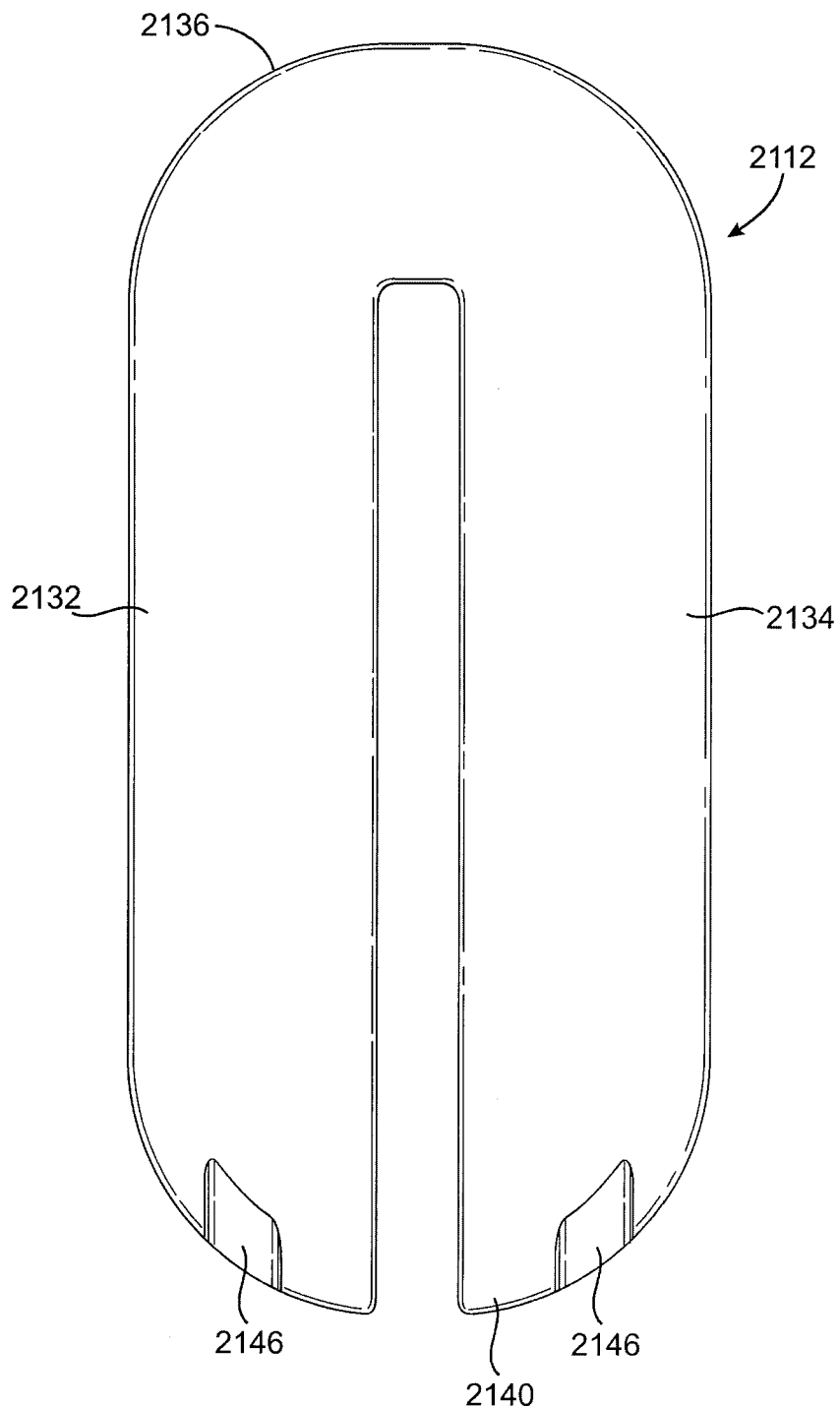
FIG. 7 is a top plan view of another embodiment of a tissue closure device constructed in accordance with the principles of the present invention.
Figure 8:
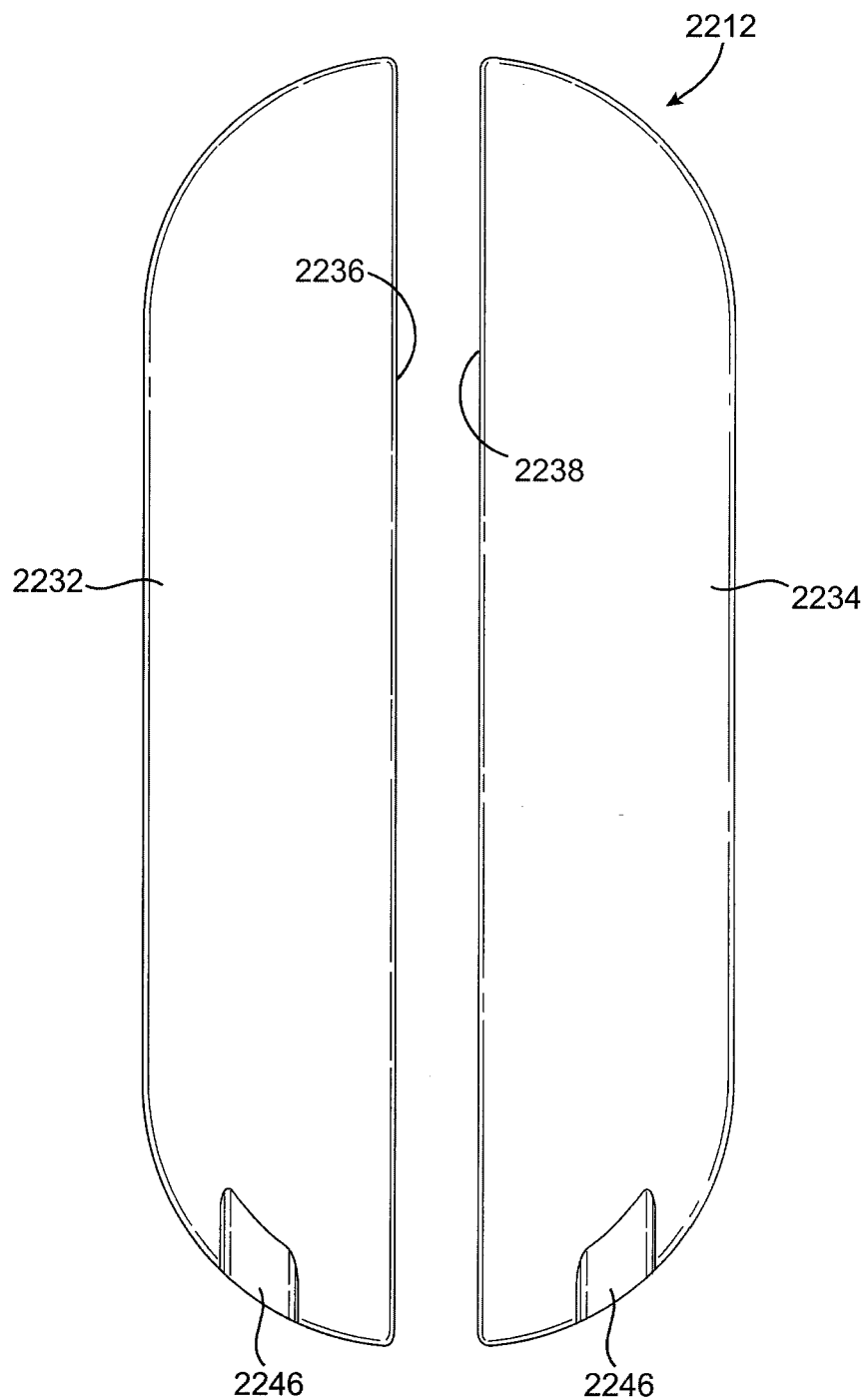
FIG. 8 is a top plan view of another embodiment of a tissue closure device constructed in accordance with the principles of the present invention.

Referring now to FIGS. 6-8, different embodiments of the tissue closure device of the present invention will be described. In FIG. 6, a tissue closure device 2012 comprises first and second legs 2032 and 2034 having ports 2046 which are constructed generally as described above with respect to tissue closure device 12. In contrast to tissue closure device 12, however, the device 2012 will not be formed as a continuous ring, but instead will be two legs 2032 and 2034 which are joined at their base but which are unattached at their distal end 2036. Tissue closure device 2112, illustrated in FIG. 7, also includes first and second legs 2132 and 2134, respectively, which are generally the same as legs 32 and 34 in tissue closure device 12. In contrast to the two previous embodiments, however, tissue closure device 2112 is joined at its distal end 2136 but is not joined at its proximal end 2140. Finally, a fourth embodiment is shown in tissue closure device 2212 in FIG. 8. Tissue closure device 2212 includes a first leg 2232 and a second leg 2234, where the legs are not joined so that the tissue-engaging surfaces 2236 and 2238 are completely free of each other and only joined by the tissue fasteners after deployment through tissue.

Figure 9:
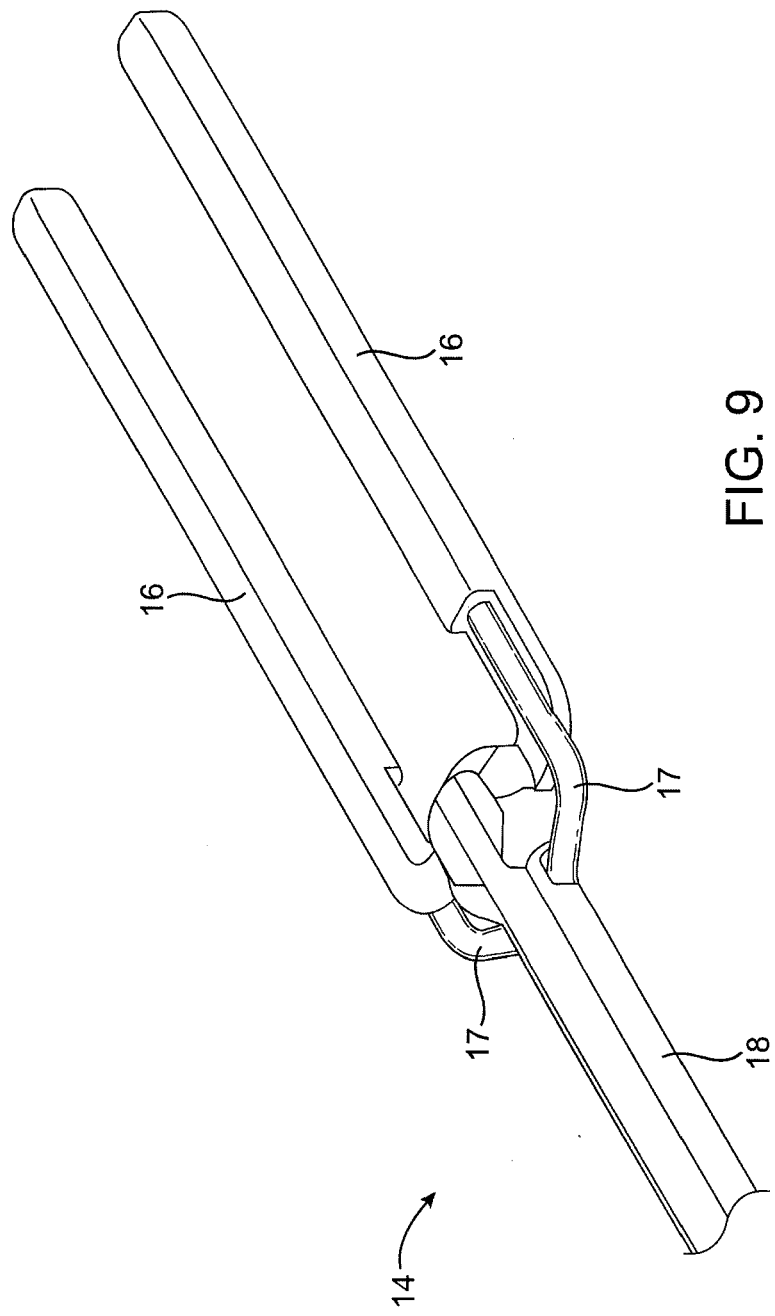
FIG. 9 is a detail of the distal end of the tissue applicator device of FIG. 1.
Figure 10:
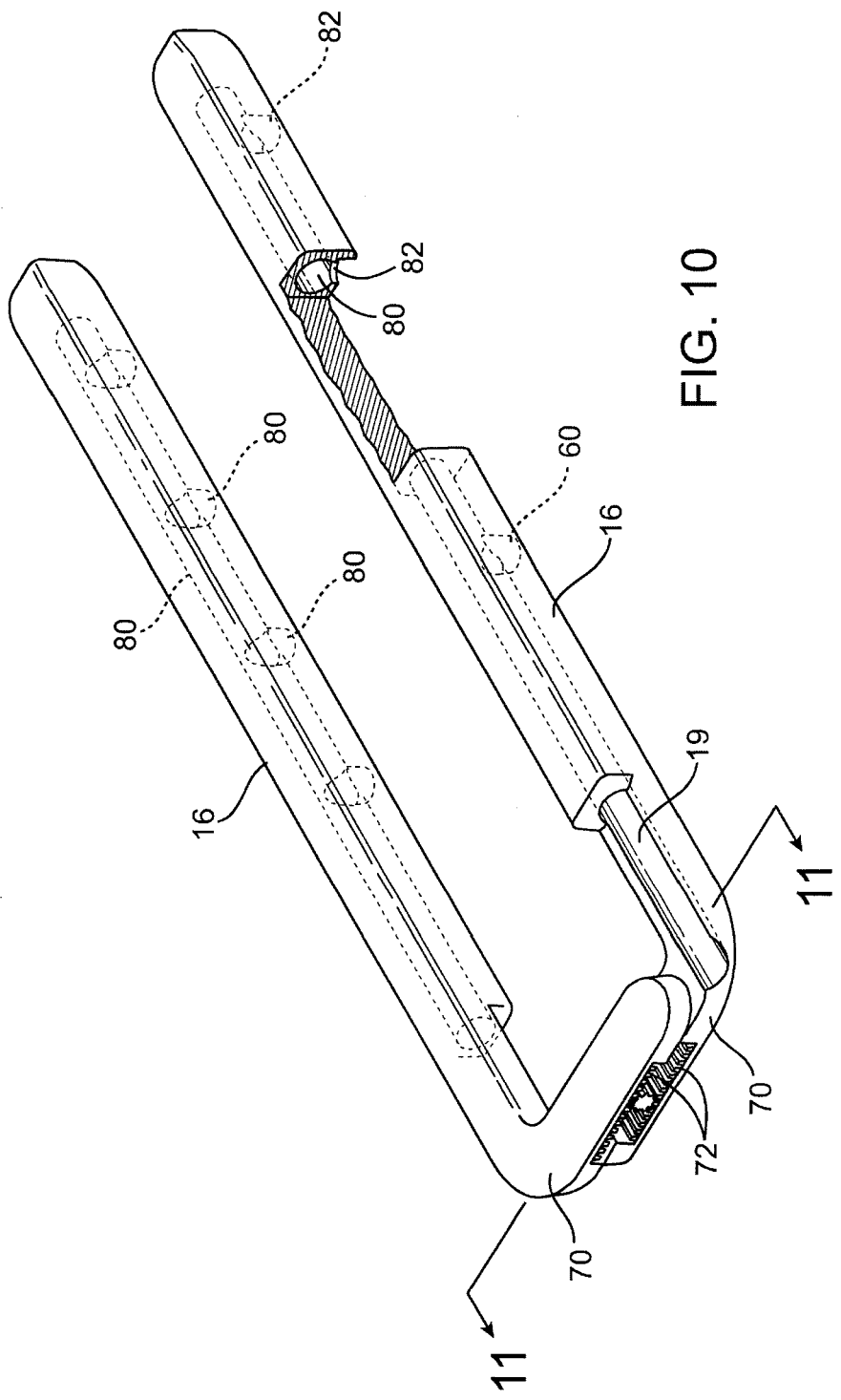
FIG. 10 is a detailed view of the distal end of the tissue closure device of FIG. 1, shown with a portion broken away and with the actuation mechanism exposed.
Figure 11:
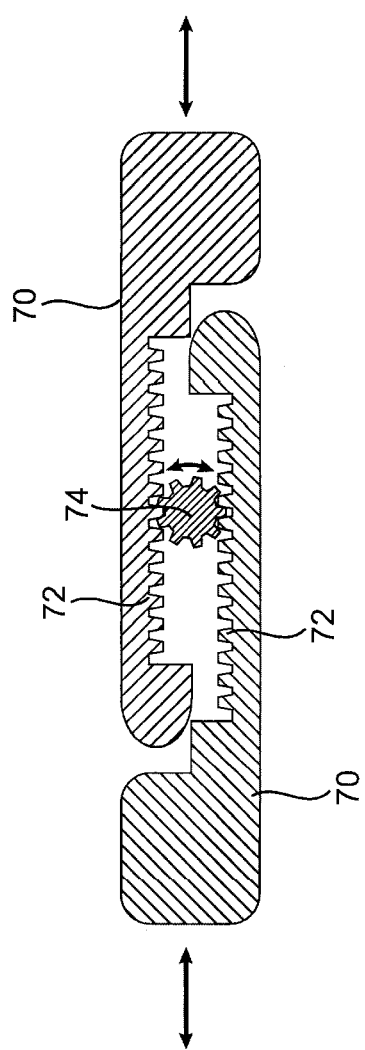
FIG. 11 is a detailed view of the device actuation mechanism taken along line 11-11 of FIG. 10.

Referring now to FIGS. 9-11, a mechanism for laterally actuating parallel probes 16 at the end of shaft 18 of the tissue closure applicator 14 will be described. The proximal end 70 of each probe 16 is formed with an L-shaped structure having gear teeth 72 along each base 70. A rotary gear 74, which is disposed in shaft 18, is disposed between the teeth 72 to form a rack-and-pinion structure, as best seen in FIG. 11. Thus, rotation of the shaft 74 in a first direction causes the probe 16 to move apart in a parallel fashion, while rotation in the opposite direction causes the probe 16 to move together in a parallel fashion. Rotation of the gear 74 can be effected by the trigger 24 on handle 20 in a conventional manner. As also seen in FIG. 10, vacuum passages 80 in each probe 16 are connected through open ends 19 to ports 82 in order to supply a vacuum or provide infusion to the plenums 40 and 42 in the tissue closure device 12. Connecting tubes 17 from the shaft 18 provide the necessary connectors to a lumen in the shaft. Usually, the ports 82 will be aligned with the ports 60 to provide for direction application of the vacuum or infusion.

Figure 12:
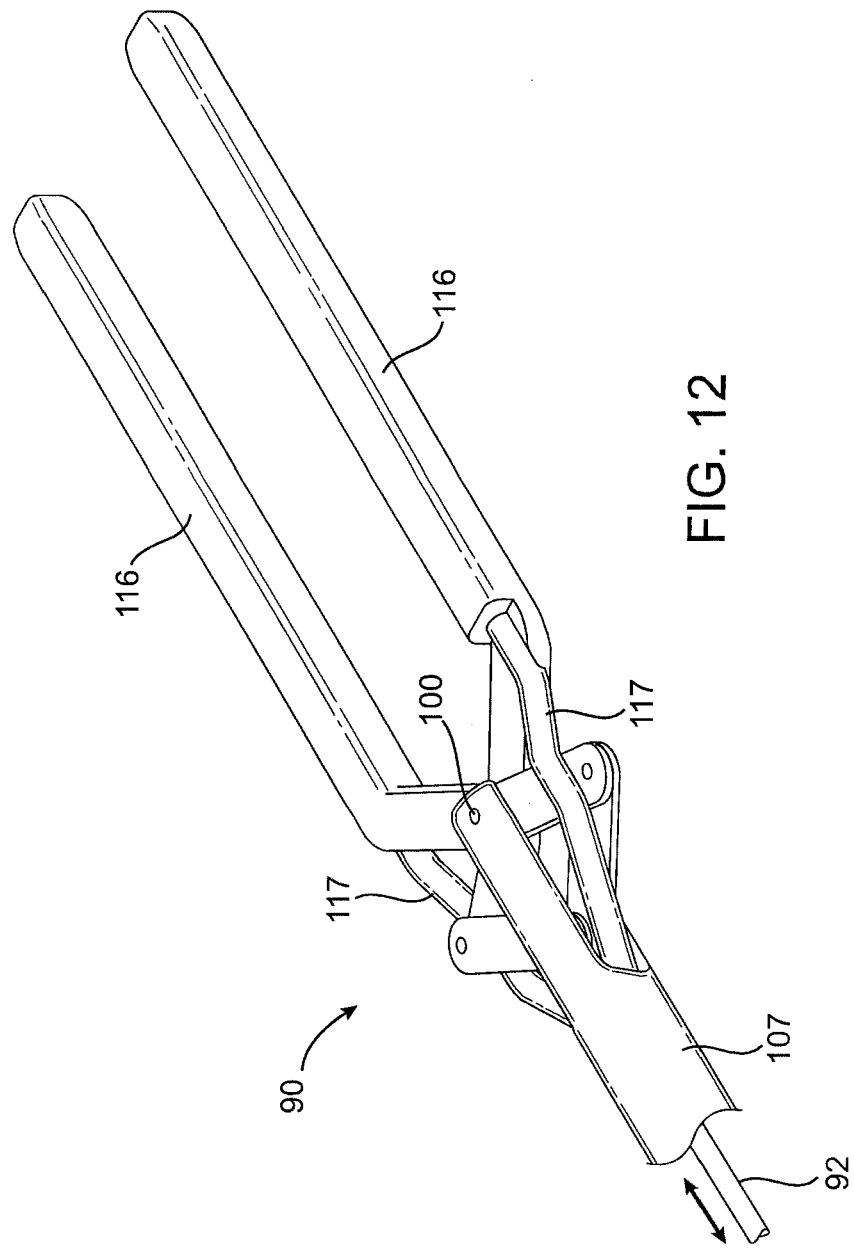
FIG. 12 illustrates another actuation mechanism for the tissue applicator of the present invention.
Figure 13:
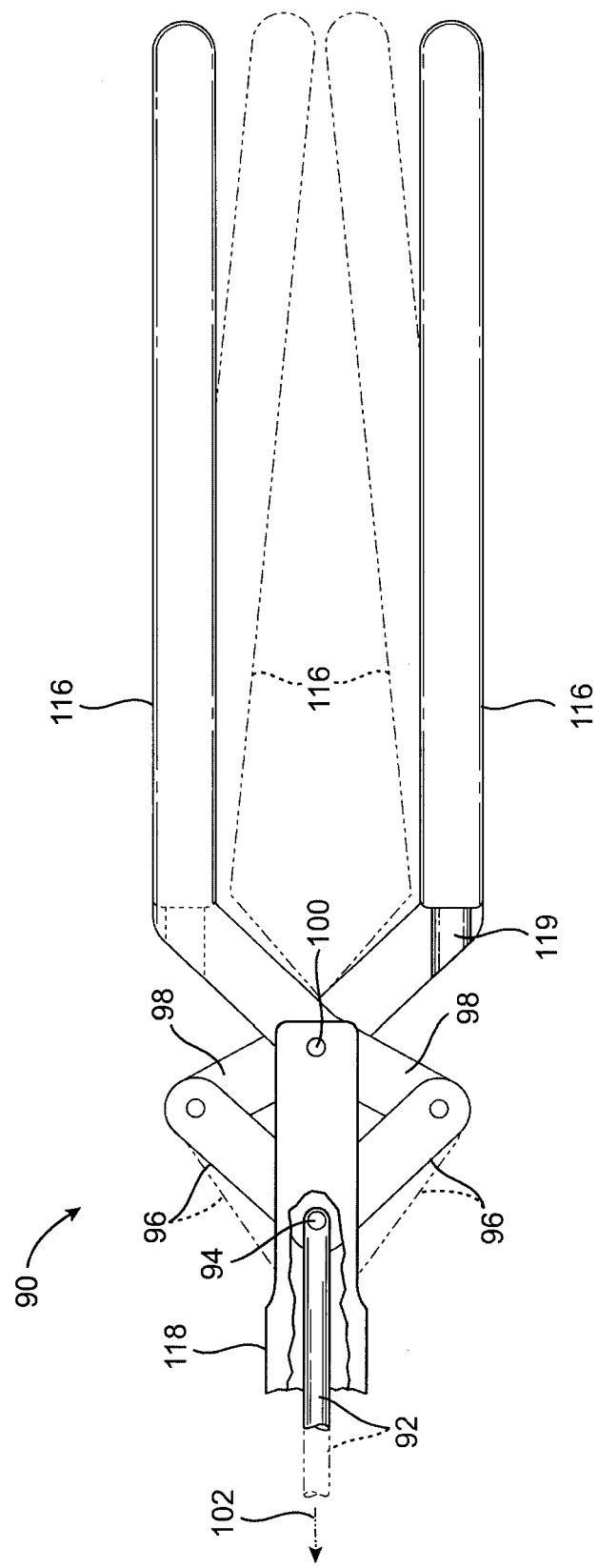
FIG. 13 is a top plan view of the embodiment of FIG. 12, shown with the open configuration in full line and in a closed configuration in broken line.

Referring now to FIGS. 12 and 13, an alternate probe actuation mechanism will be described. Probes 116 will be constructed generally the same as probe 16, as illustrated in FIG. 10, but will be attached at their proximal ends by a pivot assembly 90. The pivot assembly 90 includes a reciprocating rod 92 which is attached by a pivot pin 94 (FIG. 13) to the proximal ends of a pair of wing members 96. The distal ends of the wing members 96, in turn, are pivotally attached to lateral extensions 98 of the probes 116. The probes 116 are pivotally attached at a pivot pin 100 which is disposed on a distal end of the apparatus shaft 118. Thus, by axially reciprocating the rod 92 in a proximal direction, as shown by arrow 102 in FIG. 13, the distal ends of the wing members 96 will be closed inwardly, thus closing the probes 116, as shown in broken line in FIG. 13.

Figure 14:
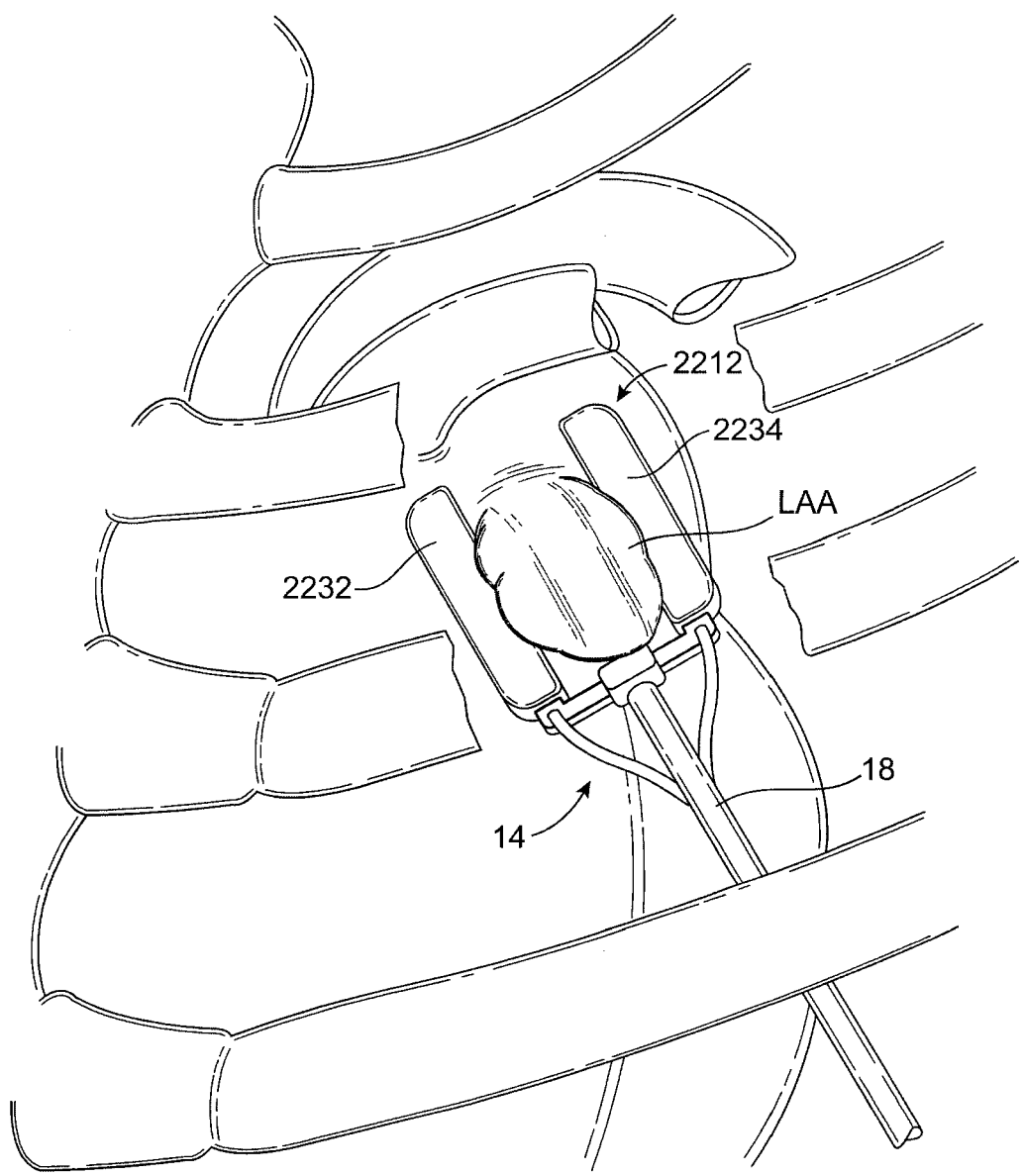
FIGS. 14, 15, 16, and 17 illustrate use of the apparatus of the present invention for implanting a tissue closure device about the base of a left atrial appendage in accordance with the principles of the present invention.
Figure 15:
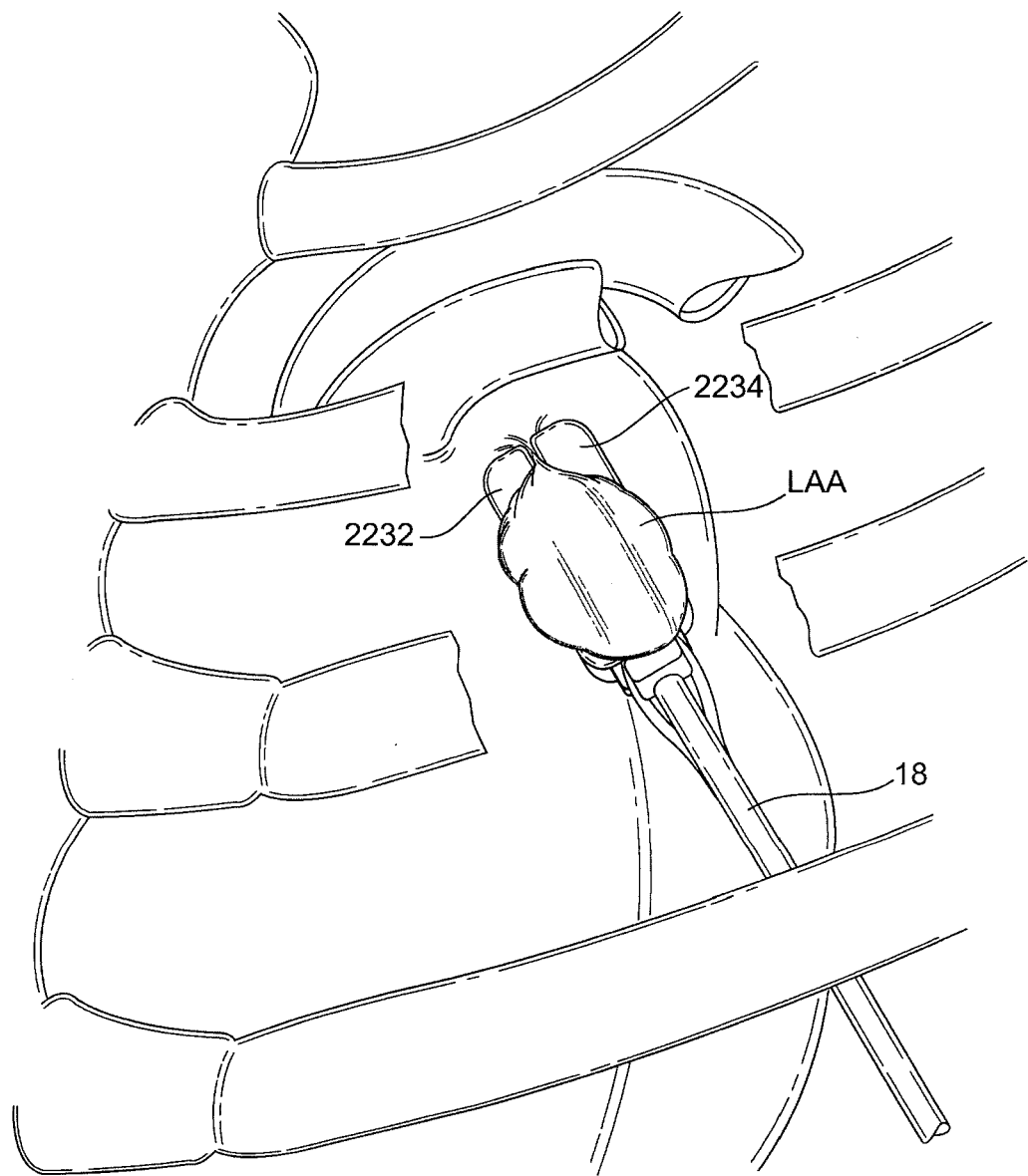
Figure 16:
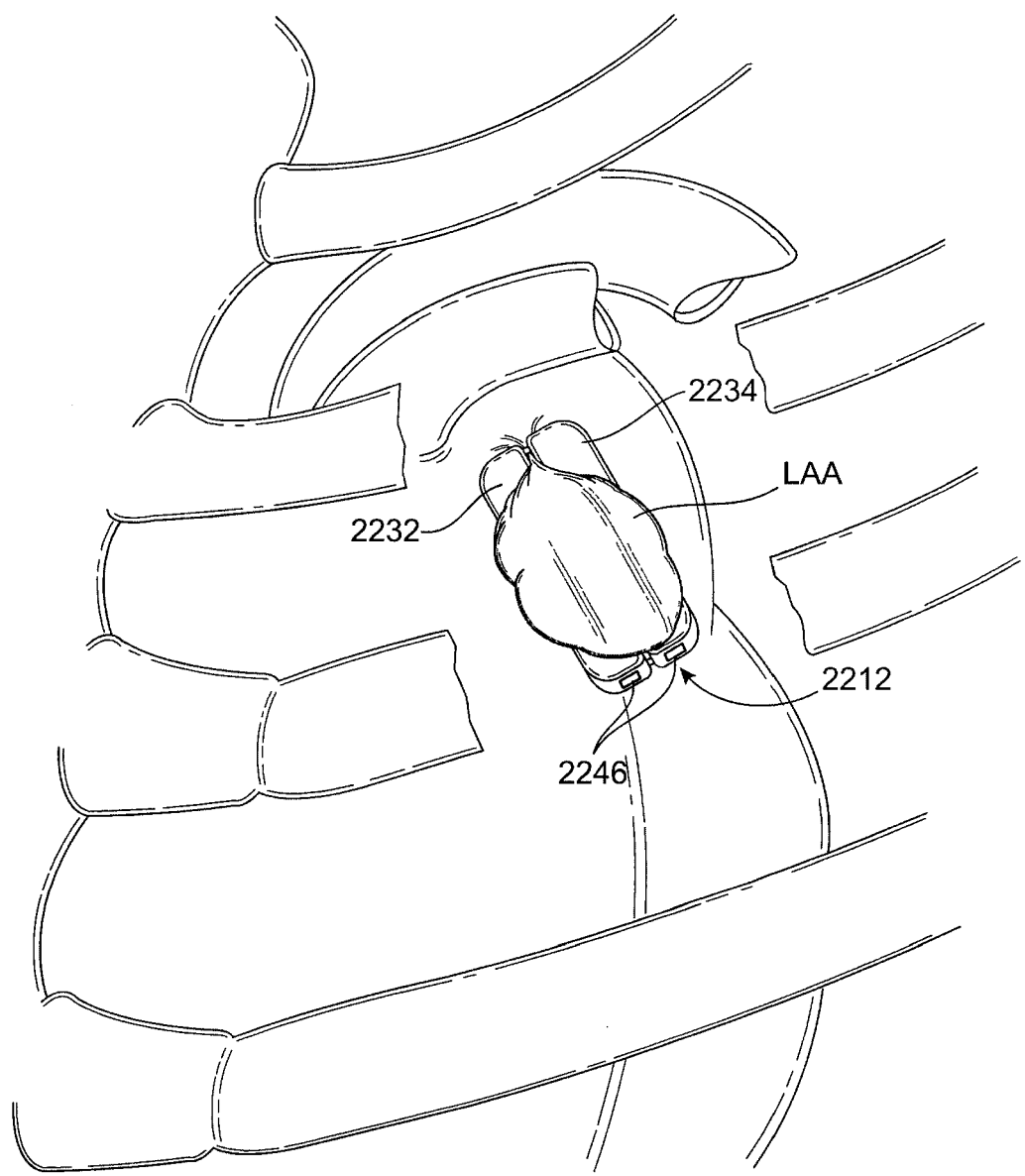

Referring now to FIGS. 14-16, use of the tissue closure system of the present invention is illustrated with respect to a procedure for implanting a tissue closure device about the base of a left atrial appendage LAA. The tissue closure device 2212 illustrated in FIG. 8 mounted on the tissue applicator 14 is illustrated, but it will be appreciated that any of the other tissue closure devices illustrated herein may be used with its respective applicator. For example, closure device 12 may be used with applicator 14. The procedure may be performed thoracoscopically using a thoracoscope (not illustrated) which is introduced in the region above the left atrial appendage LAA after the left lung has been deflated. Alternatively, the procedure can be performed under direct vision through the same incision through which the shaft 18 is introduced or through a separate incision formed over the region of the left atrial appendage. In at least most if all cases, the patient's heart will remain beating during the procedure.

The shaft 18 of the tissue closure applicator 14 is introduced intercostally, typically between the third and fourth ribs and advanced toward the patient's heart. The probes 16 are then spread apart, spreading the legs 2232 and 2234 of the closure device 2212 apart as shown in FIG. 14. After the legs are located on opposite sides of the left atrial appendage LAA, the legs will be pressed downwardly on to the cardiac tissue surrounding the base of the appendage. The vacuum may then be optionally applied through the legs 2232 and 2234, adhering the legs to the cardiac surface. The shaft 18 may still be manipulated in order to assure that the legs 2232 and 2234 are in a proper position. After the proper position is visually confirmed, the probes 16 will be mechanically closed, as illustrated in FIG. 15. The closure of the legs over the base of the left atrial appendage LAA will again be visually assessed. If it appears to be properly closed, with the legs firmly pressed upon the cardiac tissue at the base and the tissue of the base being compressed without excessive folding or other discontinuities, the trigger 14 may be pulled in order to deliver the fasteners 50 into the female receptacles 54, as illustrated in FIG. 5B. At that time, the tissue closure applicator may be withdrawn, pulling the probes from the tissue closure device 2212. The tissue closure device 2212 is then left in place at the base of the left atrial appendage LAA, as best shown in FIG. 16. Usually, the portion of the left atrial appendage above the closure device 2212 will then be excised.

Figure 17:
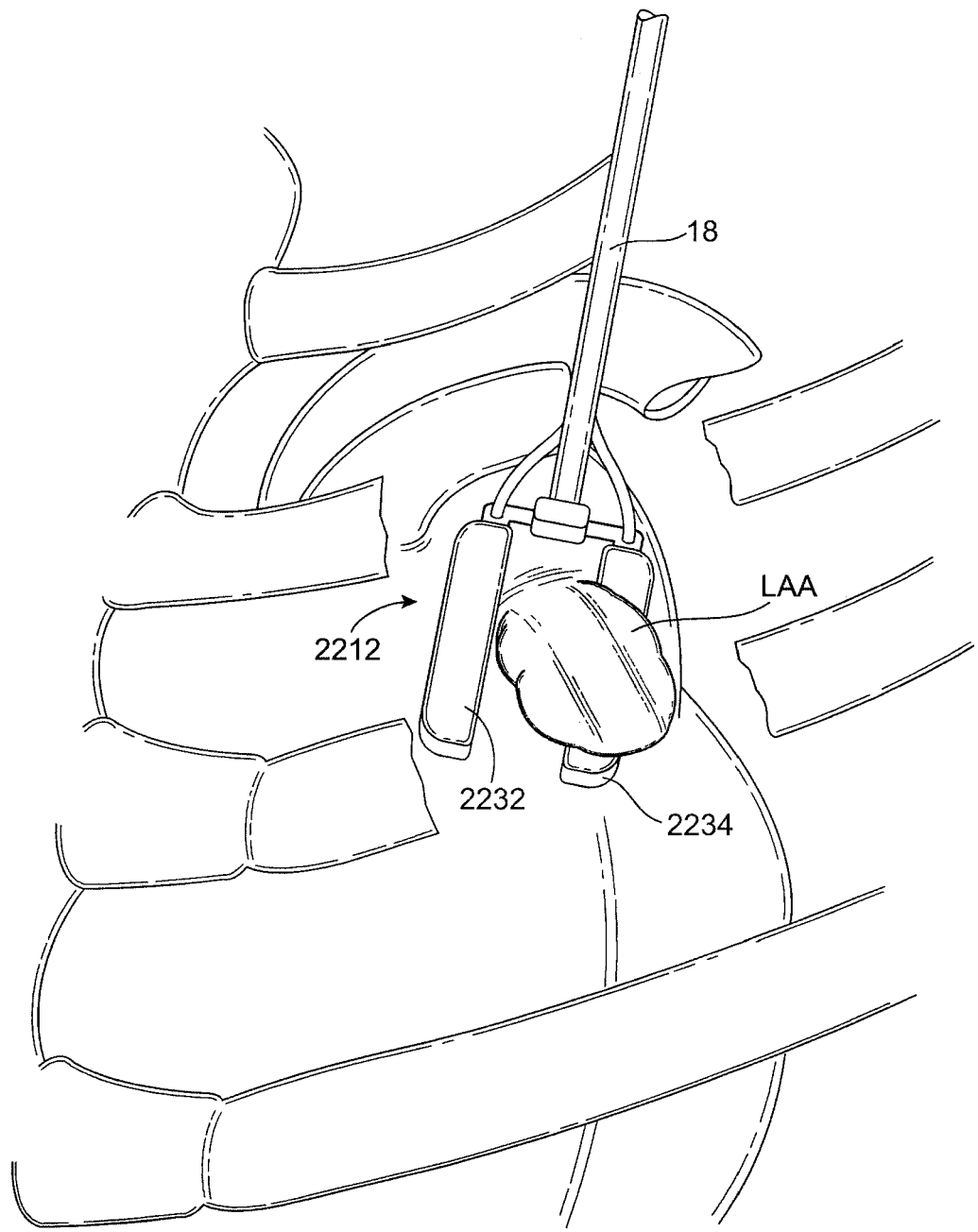

As illustrated in FIG. 17, the tissue closure device 2212 can be introduced from other directions, such as from under the clavicle to approach the left atrial appendage LAA from the top. The apparatus and procedures of the present invention could also be used in open surgical procedures, although many of the benefits associated with least invasive approaches would be lost. The most important elements of the method for closing the LAA using the present system are 1) correct placement of the device at the ostia to ensure a smooth inner closure site inside the left atrium, 2) staying off the wall of the left atrium to avoid occluding the circumflex artery, 3) creating total occlusion of the closure site, 4) eliminating suture line bleeding, and 5) choosing the correct closure device softness and compliance to eliminate erosion of the surrounding tissue.

Figure 18:
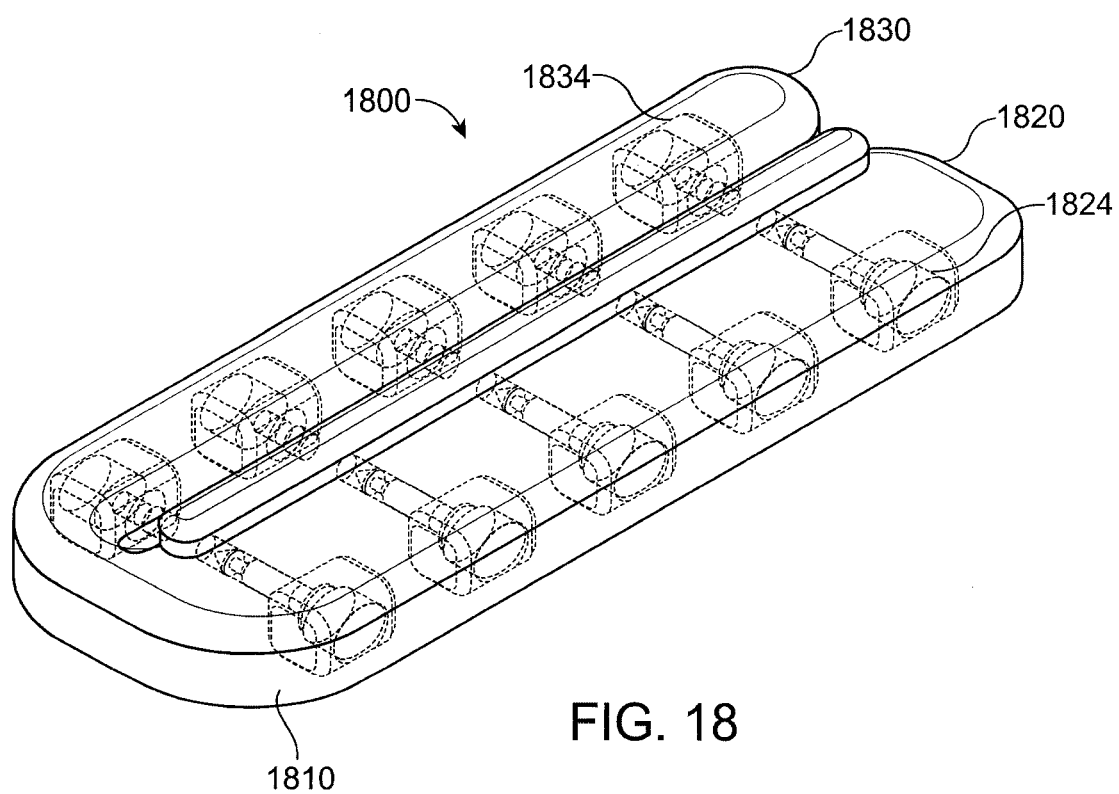
FIG. 18 is an isometric view of one embodiment of a tissue closure device constructed in accordance with the principles of the present invention.

FIGS. 18-20 illustrate another embodiment of the tissue closure device in accordance with the present invention. Tissue closure device 1800 includes a compression body 1810 formed from silicone or another soft polymer. Compression body 1810 includes opposing legs 1820 and 1830 having opposed tissue engaging surfaces 1822 and 1832. A plurality of fasteners are provided in each of the legs 1820 and 1830. As best seen in FIG. 19, a plurality of spaced-apart male fasteners 1824 are disposed within leg 1820 and corresponding female fasteners 1834 are disposed within leg 1830. As best seen in FIG. 20, leg 1820 includes a stabilizing lip 1826 extending along its entire length that helps to ensure equal pressure at the puncture site and prevent rolling displacement of leg 1820 out of its shared plane with leg 1830.

Referring to FIG. 20, male fastener 1824 includes needle barb 1825 having a sharp tip 1828 configured to pierce through tissue disposed between surfaces 1822 and 1832. Barb 1825 may include an annual groove 1825a that may be used to snap the barb into place inside the female fastener 1834. Around each barb 1825, the compression body of leg 1820 includes a well 1829 surrounding the barb in which the silicon material is removed. The diameter of well 1829 may be slightly larger than the diameter of barb 1825 such that the compression body around the well does not contact barb 1825 in an initial state. Well 1829 enables the barb 1825 to more freely translate in the vertical direction and contributes to the compliance of the surrounding compression body, which is less bound by friction to barb 1825 and more free to deform and move relative to the barb. Male fastener 1824 also includes a recess 1827 at its rear configured to create a snap fit connection with studs of the actuating comb, details of which will be discussed below. Wells 1827a are provided at the top of leg 1820 corresponding to each recess 1827 so as to allow the studs of the actuating comb to be inserted into recess 1827.

Female fastener 1834 includes a cone shaped needle barb acceptor 1836, a neck 1838, and a recess 1837. Acceptor 1836 is shaped so as to guide the tip 1828 of needle barb 1825 into the female fastener. Wells 1836a are provided in the surface 1832 of the compression body corresponding to the location of each acceptor 1836 to enable passage of barb 1825 into the female fastener. Well 1836a may be of the same diameter as well 1829. Well 1836a enables the barb 1825 to pass directly into the female fastener 1834 and improves the compliance of the compression body surrounding the barb after it has been installed. Wells 1836a and 1829 also operate in concert to create a gasket seal around the puncture site of the tissue. Once the fasteners are installed, the puncture site where barb 1825 has punctured the tissue is surrounded by well 1829 on one side and by well 1836a on the opposing side. The gasket seal captures the blood that may be released from the puncture site and prevents the blood from escaping the device. Moreover, the overall amount of bleeding may also be decreased by the pressure placed on the puncture site by the gasket seal.

Neck 1838 of the female fastener may have a diameter that is conducive for creating a snap fit when barb 1825 is inserted into female fastener 1834. For example, sharp tip 1828 of barb 1825 may pass through neck 1838 until a rear shoulder of the tip passes into recess 1837 and retains the barb 1825 in place. Recess 1837 of the female fastener accommodates the actuating comb of the present invention, which will be discussed in more detail below. Access through the compression body to recess 1837 is provided through well 1837a in the compression body that corresponds to each female fastener 1834.

Figure 21:
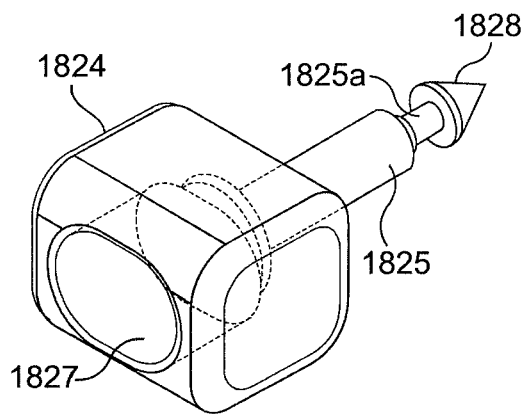
FIG. 21 is an isometric rear view of the male fastener.
Figure 22:
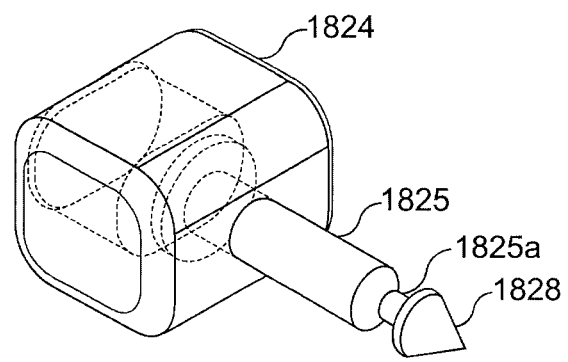
FIG. 22 is an isometric front view of the male fastener.
Figure 23:
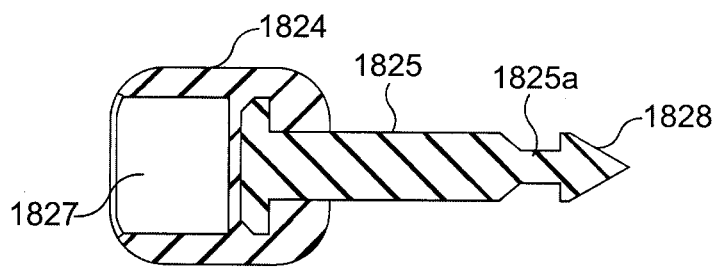
FIG. 23 is a cross-sectional view of the male fastener.
Figure 24:
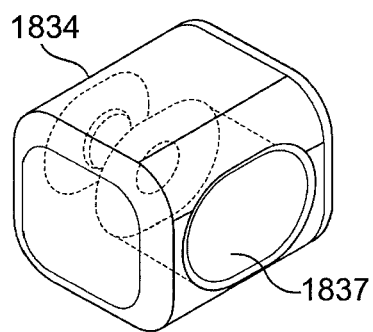
FIG. 24 is an isometric rear view of the female fastener.
Figure 25:
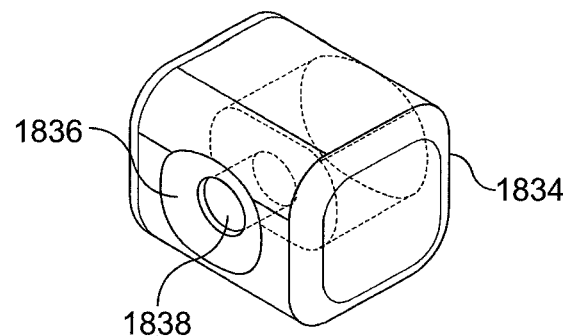
FIG. 25 is an isometric front view of the female fastener.
Figure 26:
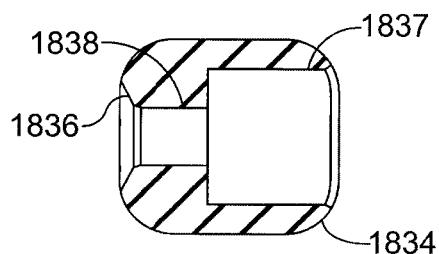
FIG. 26 is a cross-sectional view of the female fastener.

FIG. 21 provides a rear perspective view of male fastener 1824 detailing recess 1827 at its rear and barb 1825 protruding toward the front. Barb 1827 includes sharp tip 1828 and annualized groove 1825a. FIG. 22 provides a front perspective view of fastener 1824 detailing the manner in which barb 1825 protrudes from male fastener 1824. FIG. 23 provides a cross-sectional view of male fastener 1824 showing that barb 1825 may be a separate element embedded into the rear portion of fastener 1824. FIG. 24 provides a front perspective view of female fastener 1834 detailing recess 1837. FIG. 25 provides a rear perspective view detailing barb acceptor 1836 and neck portion 1838. FIG. 26 is a cross-sectional view of female fastener 1834 showing its interior construction.

Figure 27:
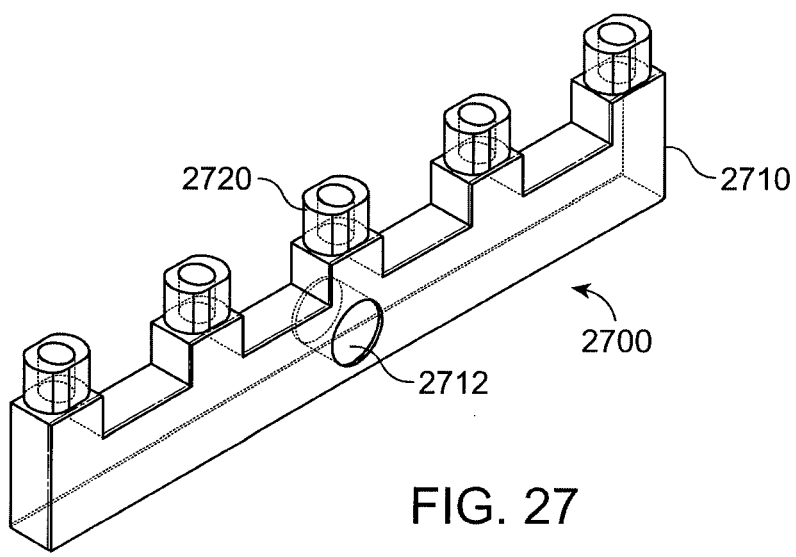
FIG. 27 is an isometric view of the alignment comb constructed in accordance with the principles of the present invention.

As mentioned previously, an alignment comb may be used with the closure device in an embodiment of the present invention. In particular, the closure device may be loaded onto a pair of opposing alignment combs to facilitate alignment between the male and female fasteners during installation. Referring to FIG. 27, each alignment comb 2700 includes a number of comb studs 2720 disposed on a body 2710. The number of studs 2720 in each comb corresponds to the number of fasteners pairs used in the tissue closure device to be installed. Body 2710 includes a dowel hole 2712 that may be used to secure the comb 2700 into an applicator of the present invention (detailed below). Stud 2720 is configured to be inserted into recesses 1827 and 1837 of the fasteners.

Figure 28:
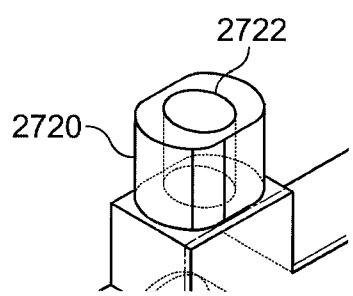
FIG. 28 is a detailed view of the comb stud.

As shown in the detailed view of FIG. 28, each stud 2720 is shaped as an oval in cross section so as to enable uniform orientation of the fasteners when the stud 2720 is inserted into the similarly oval shaped recess 1827/1837. Each stud 2720 is further configured with a taper, such that the cross section of the stud is smaller at the tip than at the base, to facilitate a "snap-fit" connection with the recesses 1827/1837. That is, the taper enables studs 2720 to be easily inserted into recesses 1827/1837 to create a friction fit, and also enable the studs to be more easily disengaged from the recesses once installation of the device is complete. Stud 2720 further includes a hollow interior channel 2722 configured to allow barb 1825 to pass into recess 1837 of the female connector 1834 when the stud 2720 is engaged with the female connector.

Figure 29:
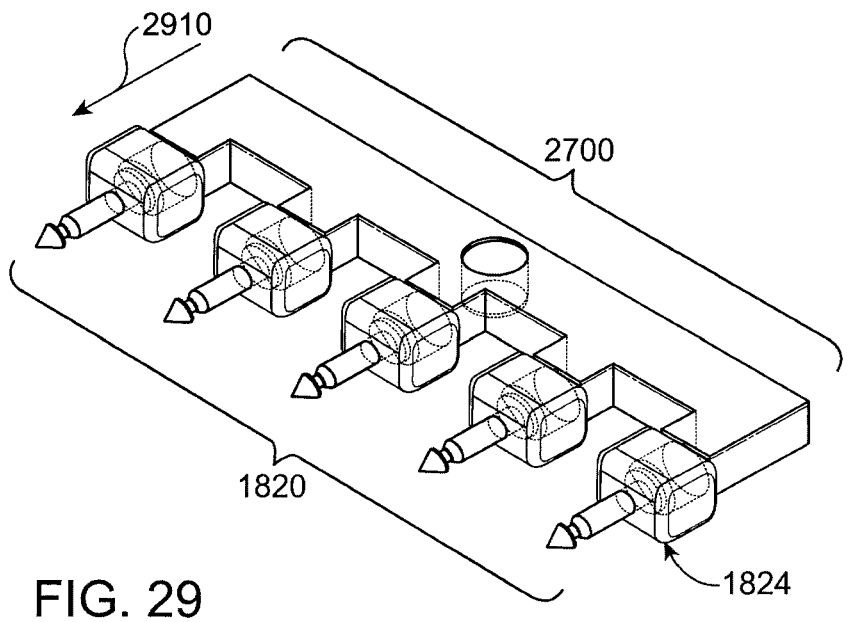
FIG. 29 is an isometric view showing the alignment comb engaged with the male fasteners of a closure device.
Figure 30:
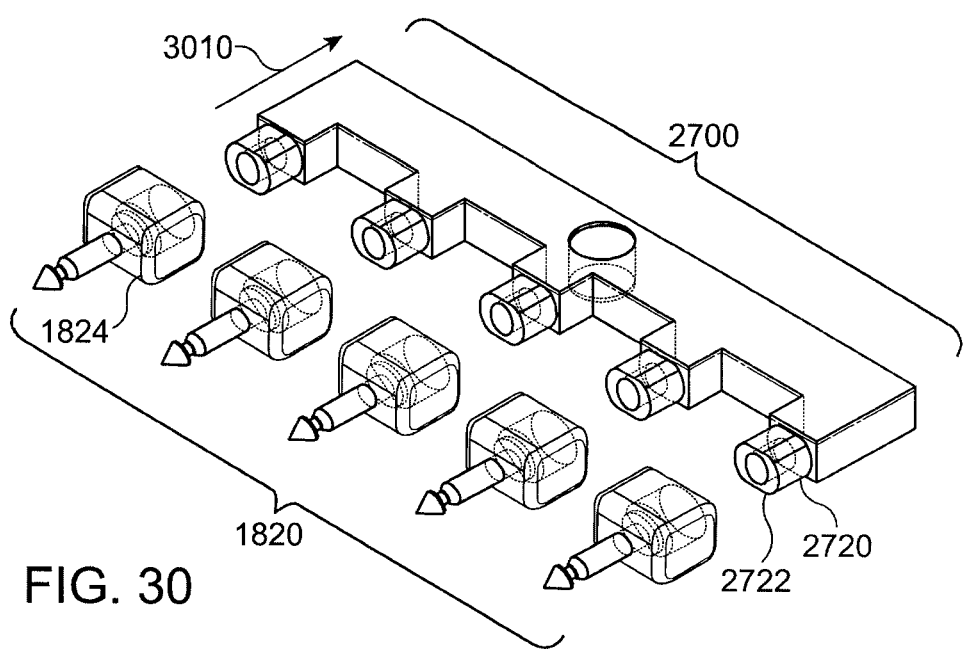
FIG. 30 is an isometric view showing the alignment comb disengaged from the male fasteners of a closure device.

FIGS. 29 and 30 illustrate how the "snap-fit" connection is used to install the tissue closure device. FIG. 29 shows a number of spaced apart male fasteners 1824 of a leg 1820 loaded onto an alignment comb 2700 (the compression body of leg 1820 has been omitted for sake of clarity). The friction fit between studs 2720 and recesses 1827 is sufficient to securely hold fasteners 1824 on the comb during the installation procedure. Studs 2720 are used to apply the installation force 2910 to fasteners 1824 so as to press the male fasteners securely into place within the female fasteners. After the installation is complete, FIG. 30 illustrates how the fasteners 1824 are ejected from the comb 2700 using a release force 3010 that does not endanger the secure engagement between installed male and female fasteners.

The foregoing generally relates to a linear embodiment of the tissue closure device in which the opposing pairs of fasteners 1824/1834 are generally disposed along a single line. Other, non-linear embodiments of the tissue closure device are contemplated by the present application and can be used to create flexible solutions to tissue closure problems. As shown in FIGS. 31A and 31B, a closure device 3100 includes a single pair of opposing fasteners 1824/1834 disposed at the geometric center of a compression body 3110. Compression body 3110 has a top portion 3120 and a bottom portion 3130 with opposing surfaces 3122 and 3132. Top and bottom portions 3120 and 3130 may be interconnected or may be independent bodies. Wells 3129 and 3136a are disposed on the top and bottom portions, respectively, to provide for a gasket seal around the puncture site. FIGS. 31C and 31D illustrate other alternative geometries for a tissue closure device. A single device with the correct geometry may be selected or manufactured to provide a customized tissue closure solution, or a combination of devices may be used to accomplish the same.

Figure 32:
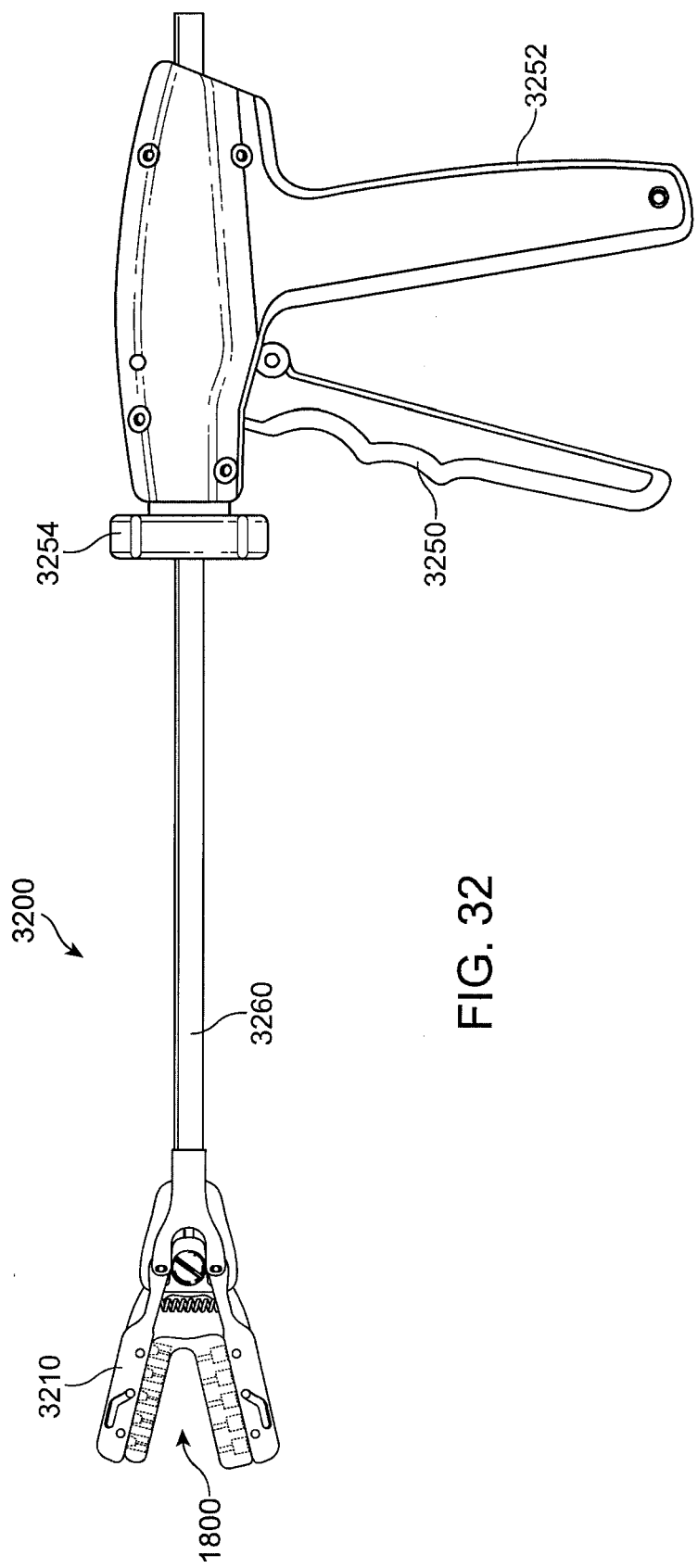
FIG. 32 is an elevation view of another embodiment of a closure device applicator constructed in accordance with the principles of the present invention.

FIG. 32 illustrates an applicator that may be used to install the tissue closure device in accordance with an embodiment of the invention. As illustrated in the FIG. 32, applicator 3200 is be loaded with closure device 1800 (using alignment combs 2700). The applicator 3200 includes a handle 3250 that is movable relative to base 3252 to actuate jaws 3210. The applicator also includes an orientation hub 3254 and an outer shaft 3260. FIG. 33A shows the applicator jaws 3210 in an open state. In particular, jaws 3210 include a set of inner jaws 3210a that are coupled to cam 3230 and capable of pivoting about the cam 3230 to close in a scissor-like manner. Cam 3230 is disposed within housing 3290 and is coupled to an inner shaft 3262 disposed coaxially within outer shaft 3260. Jaws 3210 further include a set of outer jaws 3210b that pivot at points 3282 on a base portion 3280, which is movable relative to a housing 3290 and may be coupled to the outer shaft (not shown). Outer jaws 3210b fit over inner jaws 3210a and have substantially the same position in the initial, open state of the jaws. Outer jaws 3210b may include cut-away tracks 3214 for receiving a dowel pin 3212 used to secure the alignment comb 2700 within the inner jaw 3210a. As shown in FIG. 33A, an alignment comb 2700 is fitted into each of the inner jaws 3210a.

From the open position shown in FIG. 33A, the user actuates the handle 3250 to cause inner shaft 3262 to retract into housing 3290 (in the downward direction as shown in FIGS. 33A-C). This retraction causes inner jaws 3210a to withdraw into housing 3290 and to abut against the sides of housing 3290, which causes the inner jaws 3210a to close. The movement of the inner jaws 3210a causes a corresponding retraction and closing of outer jaws 3210b, as the motion is transferred through dowel pin 3212 and track 3214. As shown in FIG. 33B, jaws 3210 are retracted into housing 3290 from the open position of FIG. 33A, and base portion 3280 has moved downward relative to housing 3290. Jaws 3210, in the closed state, cause the opposing comb studs 2720 to be disposed a set distance apart, such that male fasteners 1824 and female fasteners 1834 of the closure device 1800 loaded on the combs 2700 are securely engaged together. That is, by moving the jaws 3210 from the open state to the closed state, barb 1825 of the male fastener 1824 is caused to move toward opposing female fastener 1834, pierce the intervening tissue at the puncture site, and become securely engaged with female fastener 1834 (e.g., when sharp tip 1828 passes into recess 1837). Once the opposing male and female fasteners of the closure device have been securely engaged with each other, the successfully installed closure device is left in place when the comb studs 2720 are disengaged from the recesses 1827/1837 of the fasteners.

FIG. 33C illustrates one approach for accomplishing the disengagement motion, in which the inner shaft 3262 is actuated upward to push cam 3230 in the upward direction. Upward movement of cam 3230 causes the inner jaws 3210b to move along track 3214 upward and outward so as to release the comb studs 2720 from the recesses 1827/1837. This movement of inner jaws 3210b is independent of outer jaws 3210a. Movement of combs 2700 in a direction opposite to the direction of installation causes comb studs 2720 to disengage from the recesses 1827/1837 and frees the installed closure device 1800 from the applicator.

In some embodiments, a lasso wire may be deployed from an aperture in the distal end of a first jaw 3210 to be received and secured in a second aperture in the distal end of the other jaw 3210. The lasso wire may be of a hemispherical shape when deployed and serves to constrain the tissue to be secured between jaws 3210. In some instances, as jaws 3210 come together to install the closure device, the intervening tissue may experience a tendancy to slip toward the distal end of the jaws and out of the area between the jaws 3210. The lasso wire prevents such movement by the tissue. In some embodiments, jaws 3210 may be disposed in a plane offset from the plane of shaft 3260 by a predetermined rotation. The plane of jaws 3210 may be offset from the plane of shaft 3260 by 10 to 45 degrees, and preferably by 10 to 25 degrees.

Figure 34A:
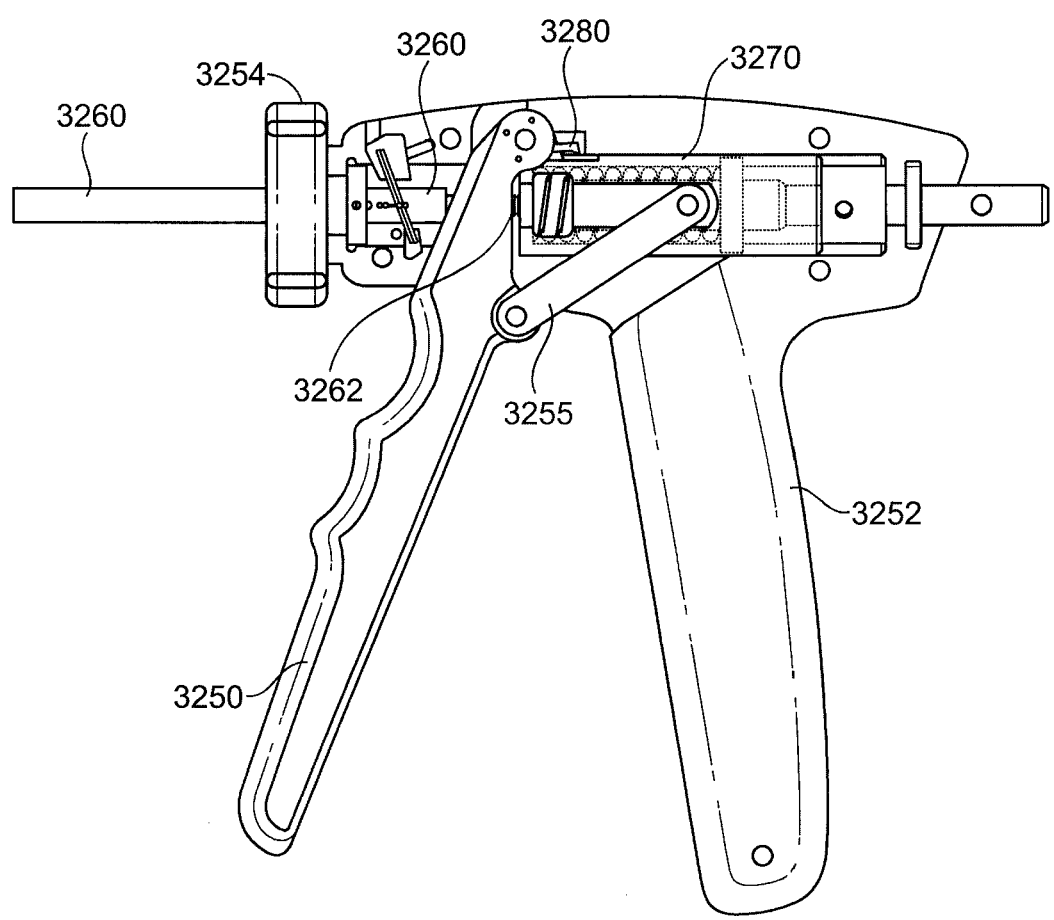
FIG. 34A is an elevation view showing the handle of the applicator in an open state.
Figure 34B:
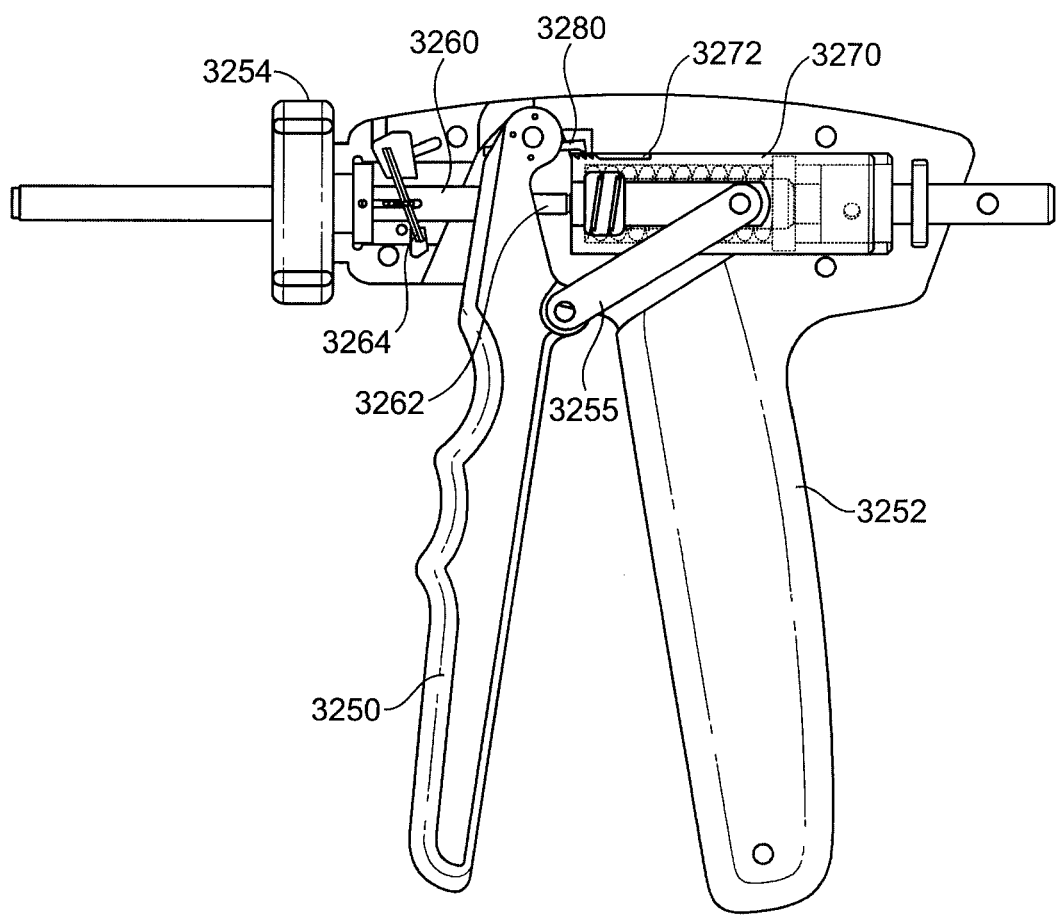
FIG. 34B is an elevation view showing the handle of the applicator in an intermediate state.
Figure 34C:
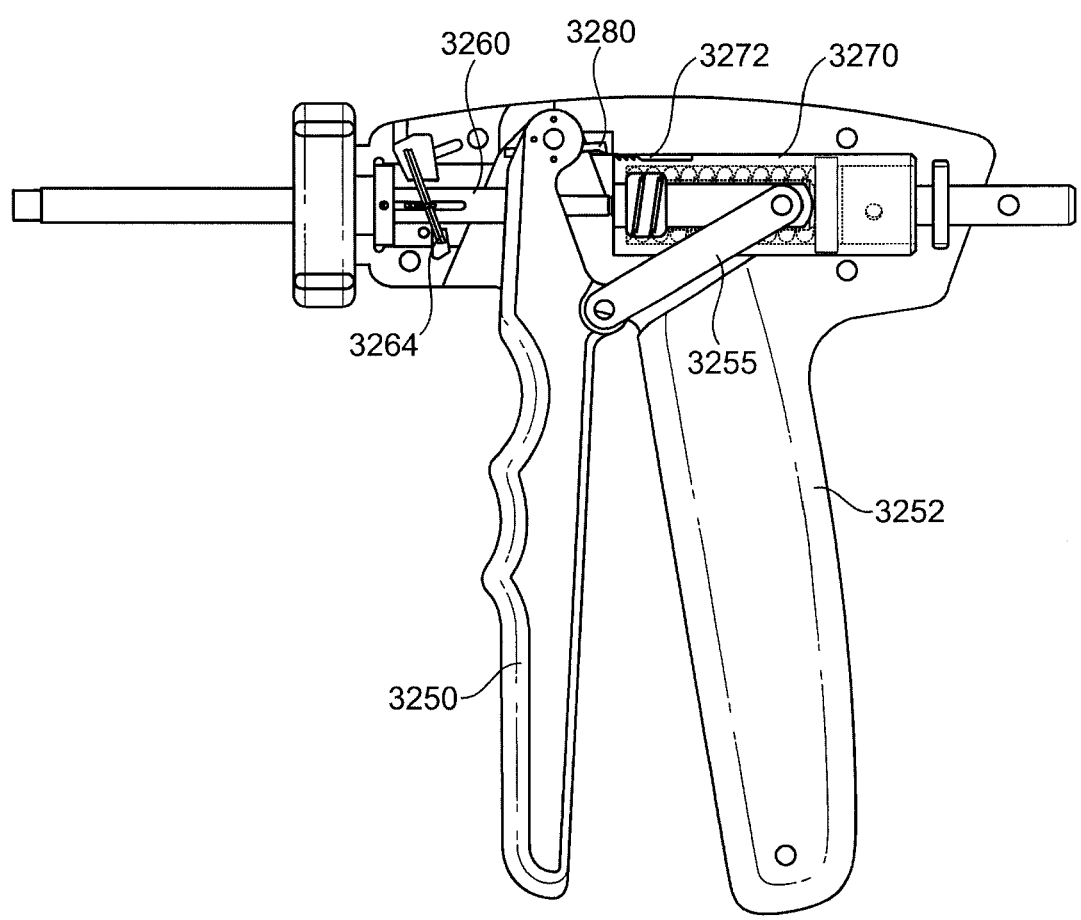
FIG. 34C is an elevation view showing the handle of the applicator in a final state, in which the jaws are first closed to install the closure device, and then the inner jaws are moved independently to disengage the comb studs from the closure device.

FIGS. 34A-C illustrate how the handle portion of the applicator 3200 actuates the jaws 3210. FIG. 34A shows an initial position of the handle portion in which jaws 3210 are open (as shown in FIG. 33A). Outer shaft 3260 is keyed to hub 3254 so as to enable rotation of the jaws about the axis of shaft 3260 when hub 3254 is rotated. Shaft 3260 is, however, slideable relative to hub 3254 along the axis of the shaft. Inner shaft 3262 is disposed coaxially within outer shaft 3260 and is coupled to trunnion 3270, which may be spring-biased to its current position. Handle 3250 is coupled to trunnion 3270 via link 3255. Handle 3250 may also include a spring biased arm 3280 that is biased downward to contact the upper surface of trunnion 3270. When handle 3250 is pulled back and actuated, trunnion 3270 and inner shaft 3262 are caused to retract (to the right in FIG. 34B), and by transferred movement of the inner jaws 3210a to the outer jaws 3210b, outer shaft 3260 (coupled to the outer jaws 3210b) are also caused to retract by a corresponding displacement. As shown in FIG. 34B, spring-biased arm 3280 enters a series of ratchet teeth 3272 disposed on the top surface of trunnion 3270, which prevents the trunnion from returning to its spring-biased position of FIG. 34A. Prior to engaging teeth 3272, displacement of the trunnion 3270 caused by the actuation of handle 3250 are undone when handle 3250 is released. As shown in FIG. 34C, handle 3250 is then pulled to its final position to install the closure device by moving arms 3210 together (as shown in FIG. 33B). In this position, inner shaft 3262 and outer shaft 3260 are at their rearmost position. Locking plate 3264 is used as a one way clutch to secure outer shaft 3260 at its rearmost position. As shown in FIG. 34C, arm 3280 has now exited the ratchet teeth 3272, which enables spring-biased trunnion 3270 to move forward along with coupled inner shaft 3262. This forward movement of the inner shaft 3262 independent of outer shaft 3260 actuates the movement of inner jaws 3210a independent of outer jaws 3210b, as shown in FIG. 33C.

While the above is a description of the preferred embodiments of the invention, various alternatives, modifications, and equivalents may be used. Therefore, the above description should not be taken as limiting the scope of the invention which is defined by the appended claims.

What is claimed is:

1. A method for closing a tissue structure, said method comprising:
    positioning a compression body over the tissue structure with at least two compliant tissue-engaging surfaces engaging opposite sides of the structure;
    deploying fasteners from at least one of said surfaces, through the tissue, and into the other surface to close the tissue structure, wherein the fasteners are deployed to close the tissue-engaging surfaces against the tissue with a pressure in the range from 0.25 psi to 20 psi.

2. A method as in claim 1, wherein the tissue structure is a left atrial appendage.

3. A method as in claim 2, wherein positioning comprises intercostally advancing the compression member.

4. A method as in claim 2, wherein positioning comprises carrying the compliant compression body on an applicator, spreading the tissue-engaging surfaces using the applicator, and closing the spread legs over the tissue structure before applying the vacuum.

5. A method as in claim 1, wherein deploying fasteners comprises advancing male elements from either or both of the tissue-engaging surface(s) to female elements in the opposed tissue-engaging surface.

6. A method as in claim 1, wherein deploying fasteners comprises advanced barbed needles from one tissue-engaging surface to the other tissue-engaging surface.

7. A method as in claim 1, further comprising viewing the tissue structure through an optical scope during at least a portion of the procedure.

8. A method as in claim 1, further comprising directly viewing the tissue structure through a percutaneous opening during at least a portion of the procedure.

9. A method as in claim 1, further comprising introducing a substrate to the tissue structure through the compression body.

10. A method as in claim 9, wherein the substance is an antibiotic, an antiseptic, or an anti-inflammatory.

11. A method as in claim 1, further comprising excising the tissue structure at a location above the compression body after the fasteners have been deployed.

12. A method as in claim 1, wherein the fasteners do not extend out of the compression body after deployment.

13. A method as in claim 1, wherein the closed fasteners provide an interrupted attachment that closes the tissue structure.

14. A method for closing a tissue structure, said method comprising the steps of:
    positioning a compression body over the tissue structure with at least two compliant tissue-engaging surfaces engaging opposite sides of the structure;
    applying a vacuum through the compression body to adhere the surfaces to the tissue structure; and deploying fasteners from at least one of said surfaces, through the tissue, and into the other surface to close the tissue structure while the vacuum continues to be applied, wherein the fasteners are deployed to close the tissue-engaging surfaces against the tissue with a pressure in the range from 0.25 psi to 20 psi.

15. A method as in claim 14, wherein curing the pressure is in the range from 0.25 psi to 1.5 psi.

16. A method for closing a tissue structure, said method comprising the steps of:

positioning a compression body over the tissue structure with at least two compliant tissue-engaging surfaces engaging opposite sides of the structure;

applying a vacuum through the compression body to adhere the surfaces to the tissue structure;

deploying fasteners from at least one of said surfaces, through the tissue, and into the other surface to close the tissue structure while the vacuum continues to be applied; and excising the tissue structure at a location above the compression body after the fasteners have been deployed.

\* \* \* \* \*